United States Patent [19]

Alitalo

[11] Patent Number: 5,877,020
[45] Date of Patent: Mar. 2, 1999

[54] PROMOTER FOR THE RECEPTOR TYROSINE KINASE, TIE

[75] Inventor: Kari Alitalo, Espoo, Finland

[73] Assignee: Helsinki University Licensing, Ltd., Helsinki, Finland

[21] Appl. No.: 650,598

[22] Filed: May 31, 1996

Related U.S. Application Data

[63] Continuation-in-part of Ser. No. 310,717, Sep. 22, 1994, abandoned.

[51] Int. Cl.$^6$ ..................................................... C12N 5/10
[52] U.S. Cl. ...................... 435/354; 435/371; 536/24.1; 536/24.31
[58] Field of Search .................................. 435/354, 371; 536/24.1, 24.31

[56] References Cited

U.S. PATENT DOCUMENTS 5,466,596  11/1995  Breitman et al. ...................... 435/325

FOREIGN PATENT DOCUMENTS

WO 93/14124  7/1993  WIPO .

OTHER PUBLICATIONS

Aprelikova et al., "FLT4, a Novel Class III Receptor Tyrosine Kinase in Chromosome 5q33–qter," *Cancer Research*, 52:746–748 (Feb. 1, 1992).
Armstrong et al., "Expression of tie Receptor Tyrosine Kinase in Leukemia Cell Lines," *Leukemia*, 7(10):1585–1591 (Oct., 1983).
De Vries et al., "The fms–like Tyrosine Kinase, a Receptor for Vascular Endothelial Growth Factor," *Science*, 255:989–991 (Feb. 21, 1992).
De Wet et al., "Firefly Luciferase Gene: Structure and Expression in Mammalian Cells," *Mol. Cell. Biol.*, 7(2):725–737 (Feb., 1987).
Dumont et al., "The Endothelial–Specific Receptor Tyrosine Kinase, tek, is a Member of a New Subfamily of Receptors," *Oncogene*, 8:1293–1301 (1993).
Galland et al., "The FLT4 Gene Encodes a Transmembrane Tyrosine Kinase Related to the Vascular Endothelial Growth Factor Receptor," *Oncogene*, 8:1233–1240 (1993).
Hogan et al., (eds.), *Manipulating the Mouse Embryo: A Laboratory Manual*, Cold Spring Harbor Laboratory, Cold Spring Harbor, New York, pp. 157–203 (1986).
Iwama et al., "Molecular Cloning and Characterization of Mouse TIE and TEK Receptor Tyrosine Kinase Genes and Their Expression in Hematopoietic Stem Cells," *Biochem. Biophys. Res. Comm.*, 195(1):301–309 (Aug. 31, 1993).
Kerr et al., "TGF–β1 Inhibition of Transin/Stromelysin Gene Expression is Mediated through a Fos Binding Sequence," *Cell*, 61(2):267–278 (Apr. 20, 1990).
Korhonen et al., "Endothelial–Specific Gene Expression Directed by the tie Gene Promoter In Vivo," *Blood*, 86(5):1828–1835 (Sep. 1, 1995).

Korhonen et al., "Enhanced Expression of the tie Receptor Tyrosine Kinase in Endothelial Cells During Neovascularization," *Blood*, 80(10):2548–2555 (Nov. 15, 1992).
Korhonen et al., "The Mouse Tie Receptor Tyrosine Kinase Gene: Expression During Embryonic Angiogenesis," *Oncogene*, 9(2):395–403 (Feb., 1994).
Logan et al., "Two Enhancer Regions in the Mouse En–2 Locus Direct Expression to the Mid/Hindbrain Region and Mandibular Myoblasts," *Development*, 117:905–916 (1993).
Maisonpierre et al., "Distinct Rat Genes with Related Profiles of Expression Define a TIE Receptor Tyrosine Kinase Family," *Oncogene*, 8:1631–1637 (1993).
Millauer et al., "High Affinity VEGF Binding and Developmental Expression Suggest Flk–1 as a Major Regulator of Vasculogenesis and Angiogenesis," *Cell*, 72:835–846 (Mar. 26, 1993).
Miller et al., "A Simple Salting Out Procedure for Extracting DNA From Human Nucleated Cells," *Nucl. Acids Res.*, 16(3):1215 (1988).
Nabel et al., "Gene Transfer into Vascular Cells," *J. Am. Coll. Cardiol.*, 17(6):189B–194B (May, 1991).
Oelrichs et al., "NYK/FLK–1: A Putative Receptor Protein Tyrosine Kinase Isolated From E10 Embryonic Neuroepithelium is Expressed in Endothelial Cells of the Developing Embryo," *Oncogene*, 8:11–18 (1993).
Pajusola et al., "FLT4 Receptor Tyrosine Kinase Contains Seven Immunoglobulin–like Loops and is Expressed in Multiple Human Tissues and Cell Lines," *Cancer Res.*, 52:5738–5743 (Oct. 15, 1992).
Partanen et al., "A Novel Endothelial Cell Surface Receptor Tyrosine Kinase with Extracellular Epidermal Growth Factor Homology Domains," *Mol. Cell. Biol.*, 12(4):1698–1707 (Apr., 1992).
Sarzani et al., "A Novel Endothelial Tyrosine Kinase cDNA Homologous to Platelet–Derived Growth Factor Receptor cDNA," *Biochem. Biophys. Res. Comm.*, 186(2):706–714 (Jul. 31, 1992).
Sato et al., "Tie–1 and Tie–2 Define Another Class of Putative Receptor Tyrosine Kinase Genes Expressed in Early Embryonic Vascular System," *Proc. Natl. Acad. Sci. USA.*, 90:9355–9358 (Oct., 1993).
Schnürch et al., "Expression of Tie–2, A Member of a Novel Family of Receptor Tyrosine Kinases, in the Endothelial Cell Lineage," *Development*, 119:957–968 (1993).
Schreiber et al., "Interaction of Endothelial Cell Growth Factor with Heparin: Characterization by Receptor and Antibody Recognition," *Proc. Natl. Acad. Sci. USA*, 82:6138–6142 (Sep., 1985).

(List continued on next page.)

*Primary Examiner*—James Ketter
*Attorney, Agent, or Firm*—Marshall, O'Toole, Gerstein, Murray & Borun

[57] ABSTRACT

The present application discloses promoter sequences for Tie, an endothelial cell receptor tyrosine kinase and their use in therapy and diagnosis as well as production of proteins in blood and tissues.

37 Claims, 13 Drawing Sheets

OTHER PUBLICATIONS

Schlaeger et al., "Vascular Endothelial Cell Lineage–Specific Promoter in Transgenic Mice," *Development*, 121:1089–1098 (1995).

Terman et al., "Identification of a New Endothelial Cell Growth Factor Receptor Tyrosine Kinase," *Oncogene*, 6:1677–1683 (1991).

Terman et al., "Identification of the KDR Tyrosine Kinase as a Receptor for Vascular Endothelial Cell Growth Factor," *Biochem. Biophys. Res. Comm.*, 187(3):1579–1586 (Sep. 30, 1992).

Weissman and Aaronson, "BALB and Kirsten Murine Sarcoma Viruses Alter Growth and Differentiation of EGF–Dependent BALB/c Mouse Epidermal Keratinocyte Lines," *Cell*, 32:599–606 (Feb., 1983).

Wingender, E., *Gene Regulation in Eukaryotes*, VCH Verlagsgesellschaft mbH, D–6940 Weinheim (Federal Republic of Germany) Chapter 1, pp. 13–16 (1993).

Yanofsky, C., "Transcriptional Regulation: Elegance in Design and Discovery," *Transcriptional Regulation*, McKnight et al. (eds.), Cold Spring Harbor Laboratory Press, New York, Chapter 1, pp. 3–24 (1992).

Ziegler et al., "Molecular Cloning and Characterization of a Novel Receptor Protein Tyrosine Kinase from Human Placenta," *Oncogene*, 8:663–670 (1993).

Fig. 2

PROMOTER FOR THE RECEPTOR TYROSINE KINASE, TIE

The present application is a continuation-in-part of U.S. patent application Ser. No. 08/310,717, filed Sep. 22, 1994, now abandoned.

FIELD OF THE INVENTION

The present invention relates generally to receptor tyrosine kinases and promoters thereof.

BACKGROUND OF THE INVENTION

The circulatory system is the first organ system to differentiate in the developing embryo. Kaufman, The Atlas of Mouse Development, Academic Press (1992). Embryonic and yolk sac vascular systems take form in an 8.5 day post-coitum (p.c.) mouse embryo, and a day later the heart beats regularly, circulating primitive blood cells, nutrients, and metabolic waste products. Endothelial cells covering blood vessels provide a barrier between blood and other tissues of the embryo. When organs differentiate and begin to perform their specific functions, the phenotypic heterogeneity of endothelial cells increases. Fenestrated vessels, nonfenestrated vessels with tight junctions and sinusoidal vessels are found, for example, in the kidney, brain, and liver, respectively. In addition, endothelial cells perform specific functions in differentiated tissue. For example, such cells take part in several biochemical and physiological events such as blood cell trafficking, blood clotting, hemostasis, ovulation, wound healing, atherosclerosis, and angiogenesis associated with tumor metastasis.

At least five receptor tyrosine kinase genes are expressed in endothelial cells. Of these, the protein products of the FLT1, KDR/FLK-1, and FLT4 genes belong to receptor tyrosine kinase subclass III; whereas Tie and its close relative Tek (Tie-2) form a novel subclass of their own (Terman, et al., *Oncogene*, 6: 1677–1683 (1991); Terman, et al., *Biochem. Biophys. Res. Comm.*, 187: 1579–1586 (1992); Aprelikova, et al., *Cancer Res.*, 52: 746–748 (1992); De Vries, et al., *Science*, 255: 989–991 (1992); Pajusola, et al., *Cancer Res.*, 52: 5738–5742 (1992); Sarzani, et al., *Biochem. Biophys. Res. Comm.*, 186: 706–714 (1992); Galland, et al., *Oncogene*, 8: 1233–1240 (1993); Millauer, et al., *Cell*, 72: 835–846 (1993); Oelrichs, et al., *Oncogene*, 8: 11–18 (1993); Schnurch and Risau, Development, 119: 957–968 (1993)).

Both human and mouse Tie cDNAs have been cloned (Partanen, et al., *Mol. Cel. Biol.*, 12: 1698–1707 (1992); Korhonen, et al., *Blood*, 80: 2548–2555 (1992); Korhonen, et al., *Oncogene*, 8: 395–403 (1994); Iwama, et al., *Biochem. Biophys. Res. Comm.*, 195: 301–309 (1993); Sato, et al., *Proc. Natl. Acad. Sci. USA.*, 90: 9355–9358 (1993)). Tie and homologous genes have been isolated from bovine and rat sources (Maisonpierre, et al., *Oncogene*, 8: 1631–1637 (1993); Sato, et al., *Proc. Natl. Acad. Sci. USA.*, 90: 9355–9358 (1993)).

The 4.4 kb Tie-encoding mRNA encodes a 125 kDa transmembrane protein which is N-glycosylated. In its extracellular domain Tie contains two immunoglobulin-like loops and three epidermal growth factor and fibronectin type III homology regions, which are followed by trans- and juxtamembrane domains connected to a tyrosine kinase domain which is split by a short kinase insert sequence and a carboxyl terminal tail (Partanen, et al., *Mol. Cel. Biol.*, 12: 1698–1707 (1992); Korhonen, et al., *Oncogene*, 8: 395–403 (1994); Sato, et al., *Proc. Natl. Acad. Sci. USA.*, 90: 9355–9358 (1993)). Both Tie and TEK have been localized to mouse chromosome 4 at a distance of 12.2 centimorgans from each other. Such receptors are uniformly expressed in endothelial cells of various blood vessels during embryonic development, although the expression of Tek mRNA appears to begin 0.5 days earlier than the expression of Tie. In adult mice, the expression of Tie mRNA persists in vessels of the lung whereas in the heart and brain it appears to decrease. Korhonen, et al., *Oncogene*, 8: 395–403 (1994). Production of Tie mRNA is enhanced during ovulation and wound healing and in human glioblastomas (Korhonen, et al., *Blood*, 80: 2548–2555 (1992)).

Endothelial cells play a key role in gene therapy directed to diseases involving endothelial cells and blood vessels, such as establishment of neovascularization or inhibition of angiogenesis, and control of inflammatory trafficking of leukocytes. One approach to the treatment of vascular disease is to express genes at specific sites in the circulation that might ameliorate the disease in situ. Because endothelial cells are found at diseased sites, they represent logical carriers to convey therapeutic agents that might include anticoagulant, vasodilator, angiogenic or growth factors. Accordingly, the genetic modification of endothelial cells represents a therapeutic approach to the treatment of many vascular disorders, including hypertension, atherosclerosis and restenosis. For example, endothelial cells expressing growth inhibitory proteins could be introduced via catheter to the angioplasty site to prevent local intimal hyperplasia and clinical restenosis. The luminal surface of vascular grafts could also be lined with genetically modified endothelial cells producing therapeutic proteins which prevent thrombosis or promote repopulation (Nabel, et al., *J. Am. Coll. Cardiol.*, 17: 189B–194B (1991)).

Endothelial cells lining blood vessels are easily transfected with methods using liposomes, adenovirus vectors and retroviral vectors (Nabel, et al., *J. Am. Coll. Cardiol.* 17: 189B–94B). Endothelial cells are also in direct contact with blood and are therefore optimal sources for production and secretion of desired proteins or peptides into the blood stream. For example, the Factor VIII gene may be introduced into endothelial cells under an endothelial-cell-specific promoter, resulting in correction of hemophilia if the protein were expressed in sufficeint quantity. On the other hand, endothelial cells are also useful for delivery of peptides or proteins expressed in them into tissues. In this regard, a selective expression of a particular gene regulatory element in endothelial cells of the microvasculature (capillaries) is extremely useful, given that most of the cell surface area facing the vascular lumen consists of microvascular endothelial cells.

Control elements of the endothelial-cell-specific promoters may be further subdivided and dissected into functional elements and units according to methods standard in the art. The Tie protein is expressed in certain endothelial cells and in a small fraction of human bone marrow cells including hematopoietic progenitor cells. See Batard et al., *Blood*, 68:1729–1735 (1996). Therefore, it is likely that the Tie promoter is active also in some hematopoietic cells. However, expression of the Tie promoter in hematopoietic cells may be controlled by elements which are distinguishable from endothelial-cell-specific elements and may be dissected away while retaining the endothelial cell specificity of the promoter.

The present invention provides a novel promoter associated with the gene encoding the Tie receptor tyrosine kinase for use in therapeutic and diagnostic procedures. In addition, the promoter may prove useful in the production of desired proteins to the blood or tissues of animals.

SUMMARY OF THE INVENTION

The present invention generally relates to promoter sequences for the receptor tyrosine kinase, Tie. In one aspect, the invention provides a purified and isolated DNA comprising a promoter for a mammalian Tie receptor tyrosine kinase. For example, the invention provides a purified and isolated DNA comprising a promoter for a mouse Tie receptor tyrosine kinase. The invention further provides a purified and isolated DNA comprising a promoter for a human Tie receptor tyrosine kinase. In a preferred embodiment of the invention, a mouse Tie promoter is provided comprising the sequence shown in SEQ ID NO: 1. Also in a preferred embodiment, a human Tie promoter is provided comprising the sequence shown in SEQ ID NO: 2.

The invention also is directed specifically to DNAs comprising those portions of the foregoing sequences which are capable of promoting transcription of a gene operably linked thereto, e.g., in a transfected endothelial cell or bone marrow cell. Illustrative portions having promoter activity are exemplified herein, such as a portion corresponding to nucleotides 1408 to 1517 of SEQ ID NO: 1, a portion corresponding to nucleotides 1274 to 1517 of SEQ ID NO: 1, and a portion corresponding to nucleotides 730 to 1517 of SEQ ID NO: 1. Synthesis and screening procedures are disclosed herein for demonstrating promoter activity in homologous portions of SEQ ID NO: 2 and for demonstrating promoter activity in other portions of SEQ ID NOs: 1 and 2 which are not specifically exemplified herein. Each discrete portion of the sequences described herein which is capable of promoting transcription of a protein-encoding DNA operably linked thereto is intended as an aspect of the invention.

A promoter according to the invention drives the expression of endothelial cell receptor tyrosine kinases, and in particular, the receptor tyrosine kinase, Tie.

In a related aspect, the invention provides vectors comprising promoters of the invention. Thus, in one embodiment, the invention provides a vector comprising a mouse Tie receptor tyrosine kinase promoter, and in another embodiment, the invention provides a vector comprising a human Tie receptor tyrosine kinase promoter. A vector according to the present invention may be any vector suitable for incorporating a promoter according to the invention. A preferred vector of the invention comprising a mouse Tie receptor tyrosine kinase promoter is vector 0.73mTIEpromGL2, deposited on Sep. 19, 1994, with the American Type Culture Collection (ATCC), 12301 Parklawn Drive, Rockville, Md. 20852, and having ATCC accession number 75892. A preferred vector of the invention comprising a human Tie receptor tyrosine kinase promoter is vector 5.0hTIEpromSDK-LacZ, deposited on Sep. 19, 1994, with the ATCC and having ATCC accession number 75893.

In another aspect, the invention provides host cells transfected with DNAs or vectors of the invention. Host cells according to the invention may be any host cell capable of housing the promoter or a vector containing the promoter according to the invention. Preferred host cells include mammalian cells wherein Tie mRNA expression is detectable, e.g., endothelial cells. Examples of host cells according to the invention are LEII endothelial cells.

In yet another aspect, the invention is directed to a chimeric gene comprising a Tie receptor tyrosine kinase promoter of the invention. Chimeras of the invention are DNA constructs wherein a Tie receptor tyrosine kinase promoter of the invention is linked to a DNA other than the Tie receptor tyrosine kinase-encoding DNA with which the promoter is naturally associated, in a manner whereby the promoter is capable of promoting transcription of the linked DNA. An exemplary chimeric gene is a promoter of the invention operably linked to a reporter gene and/or any other gene encoding a protein of interest (e.g., a hormone), such chimeric genes being useful in the production of the encoded proteins when the chimeric gene is transfected into appropriate host cells, such as endothelial cells.

In another aspect, the invention provides methods of expressing a gene in a transfected mammalian cell, and in particular a transfected endothelial or bone marrow cell. In a preferred method for expressing a gene of interest, a promoter of the invention that is operably linked to the gene is transfected into a mammalian cell, e.g., a mammalian endothelial cell or a mammalian fertilized oocyte (zygote). The cell is maintained, cultured, propagated, etc. under conditions wherein the promoter of the invention promotes expression of the gene. For example, in an embodiment wherein the transfected cells are embryonic stem cells, the cells are transferred into appropriate female host(s) under conditions to permit generation of transgenic animal(s). The promoter of the invention promotes expression of the gene in, e.g., endothelial cells of the transgenic animals.

Other aspects, advantages, and uses of the invention will be apparent upon consideration of the following Detailed Description thereof.

DESCRIPTION OF THE DRAWINGS

The file of this patent contains at least one drawing executed in color. Copies of this patent with color drawing(s) will be provided by the Patent and Trademark Office upon request and payment of the necessary fee.

FIG. 2 is a comparison of mouse and human Tie promoter sequences (SEQ ID NOs: 1 and 2).

FIG. 4, panel B, shows expression of a mouse Tie promoter construct in yolk sac blood islands in 8.5 day embryos.

FIG. 5, panels C and D, show the expression pattern of mouse Tie promoter in 11.5 day embryos.

FIG. 6, panel B, shows expression of the Tie promoter in 11.5 day embryonic lung tissue.

FIG. 6, panel C, shows expression of the Tie promoter in 15.5 day embryonic brain tissue.

FIG. 6, panel D, shows expression of the Tie promoter in 15.5 day embryonic liver tissue.

FIG. 6, panel E, shows expression of the Tie promoter in developing bone trabeculae.

FIG. 6, panel F, shows expression of the Tie promoter in developing kidney tissue.

FIG. 7, panel B, shows expression of the Tie promoter in the endothelial network of the bone marrow in an 8-week-old mouse.

FIG. 7, panel C, shows expression of the Tie promoter in kidney tissue of an 8-week-old mouse.

FIG. 7, panel D, shows expression of the Tie promoter in heart tissue of an 8-week-old mouse.

FIG. 7, panel E, shows expression of the Tie promoter in liver tissue of an 8-week-old mouse.

FIG. 7, panel F, shows expression of the Tie promoter in brain tissue of an 8-week-old mouse.

DETAILED DESCRIPTION OF THE INVENTION

The present invention provides promoter sequences capable of directing the expression of recombinant DNA sequences in endothelial cells. In particular, the invention provides promoter sequences which direct expression of the beta-galactosidase reporter gene in endothelial cells of mouse tissues. Promoters of the invention also are useful for production of proteins and peptides which act as anticoagulants, vasodilator inhibitors of thrombosis or restenosis into endothelial cells, blood and tissues, for example. Promoters according to the present invention are useful for directing expression of proteins and peptides for human gene therapy, antigens and markers useful for endothelial cell tagging, and antisense RNA constructs for use in endothelial cells in vivo and in vitro. Promoters, vectors, and host cells according to the invention also are useful in gene therapy for promoting expression of various growth factors or receptors or their domains. Moreover, analogs of promoters according to the invention are useful for inhibiting undesired endothelial cell proliferation as, for example, the inhibition of angiogenesis during tumor formation.

EXAMPLE I

Cloning and characterization of mouse and human genomic Tie DNAs

A. Mouse Genomic Tie

In order to characterize the genomic organization of the mouse Tie gene, approximately 3×10⁶ plaques were screened. The plaques were obtained from a genomic library made from DNA of adult SV129 mouse liver cells (Clontech). A mouse 1C1D cDNA fragment (Korhonen, et al., *Blood.*, 80:2548–2555 (1992)) encoding the epidermal growth factor homology domains

[GCVKDCPGCLHGGVCHDHDGCVCPPGFTGTRCE-QACREGRFGQSCQEQCPG TAGCRGLTFCLPDPYGC-SCGSGWRGSQCQEACAPDHFGADCRLQCQCQNGGT CDRFSGCVCPSGWHGVHCEKSDRIPQIL: SEQ ID NO: 3] was used as a probe to screen the plaques. Three separate clones, SV1, SV2, and mTie were obtained thereby and each was subcloned into pGEM 3Zf(+) (Promega) and characterized by partial dideoxy chain termination sequencing and restriction enzyme analysis.

Figure 1:
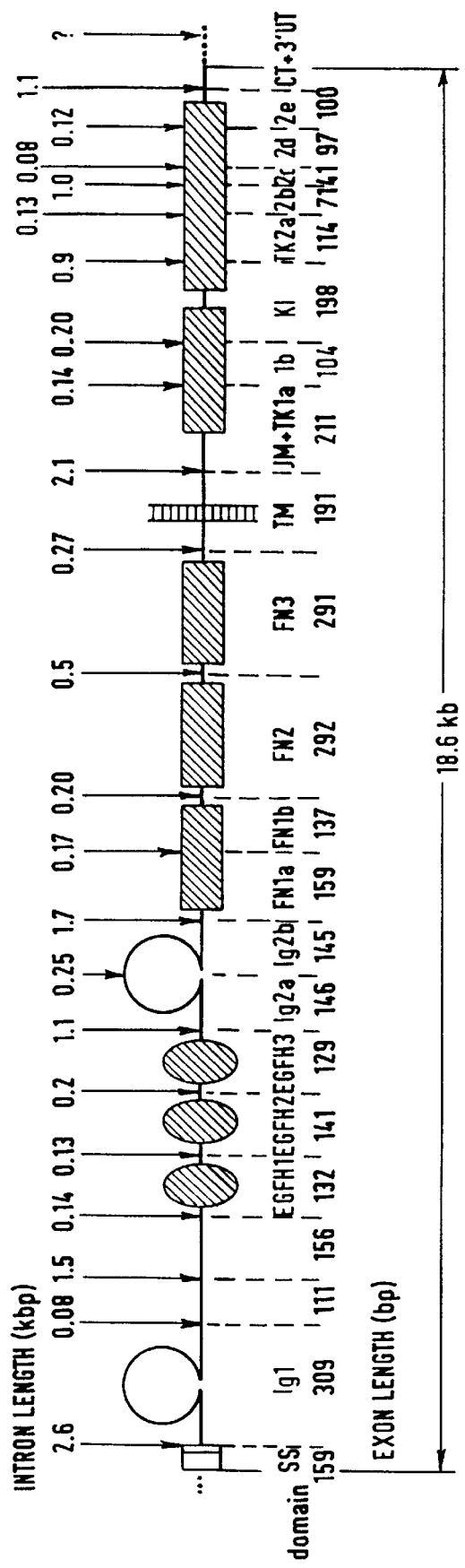
FIG. 1 is a schematic diagram of the mouse Tie gene and promoter.
Figure 2:
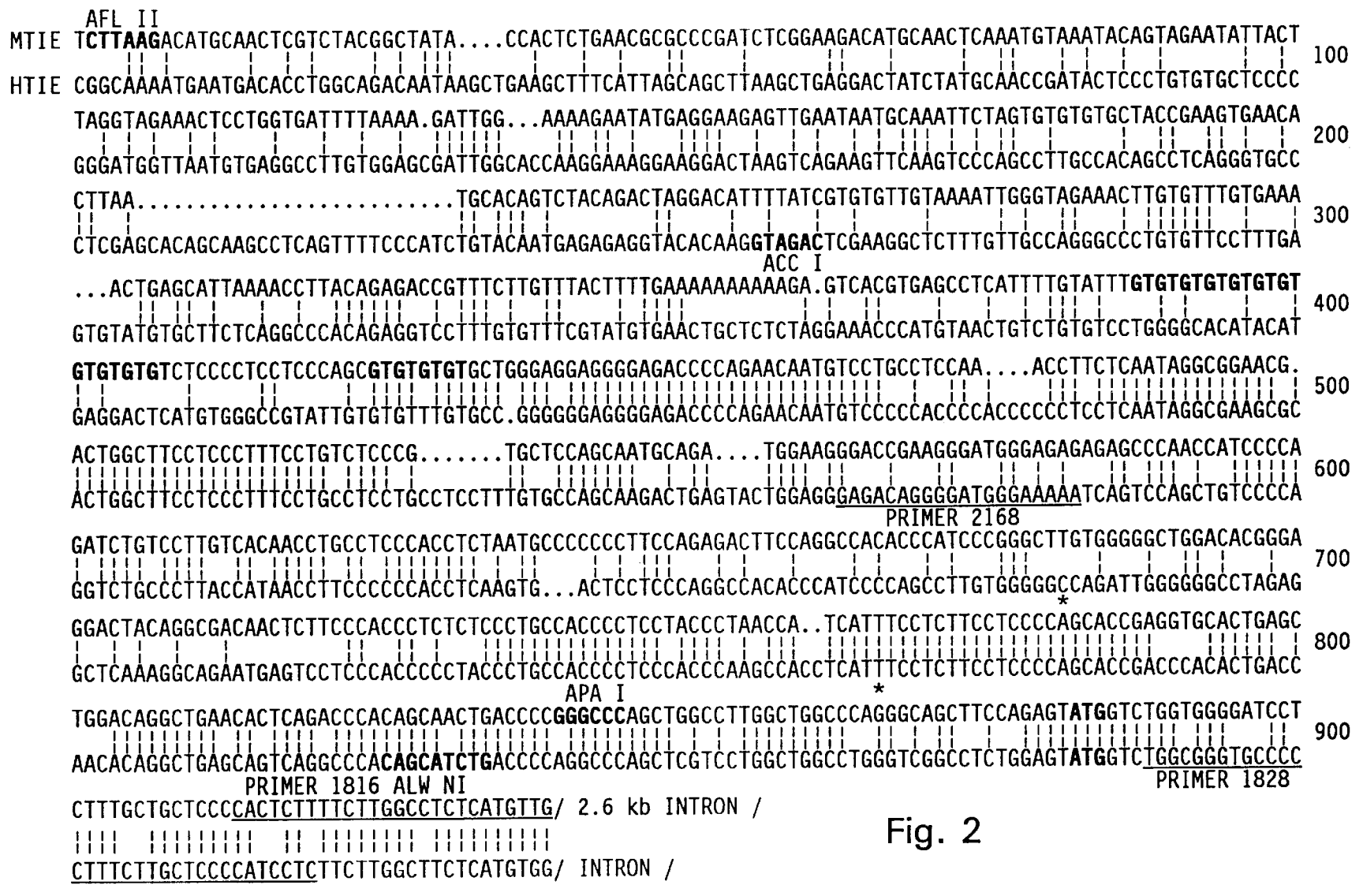

A schematic structure of the mouse Tie gene and its promoter is shown in FIG. 1. In that Figure, the positions of introns are indicated by arrows and their lengths are indicated. Restriction mapping, PCR, and nucleotide sequence analysis showed that the Tie gene spans approximately 19 kb of genomic DNA. Tie is encoded by 23 exons. The distinct structural domains of the extracellular portion are encoded by either one exon (e.g., the first immunoglobulin-like loop, epidermal growth factor homology domains 1–3, and fibronectin-like domains 2 and 3) or by two exons (e.g., the second immunoglobulin-like loop and first fibronectin-like domain). The transmembrane region is encoded by a distinct exon; whereas the tyrosine kinase domain containing the kinase insert is encoded by eight exons of which the first encodes the juxtamembrane region. The lengths of the introns vary from 80 bp to 2.6 kb. FIG. 2 depicts a mouse genomic DNA sequence extending from the 3' end of the first exon of the mouse Tie gene upstream to an AflII restriction site. This sequence, as well as additional upstream mouse genomic DNA sequence, is set forth in SEQ ID NO: 1. The mouse sequence depicted in FIG. 2 corresponds to nucleotides 729 to 1611 of SEQ ID NO: 1.

B. Human Genomic Tie

Three human Tie clones were isolated from a human placental genomic DNA library in the EMBL-3 vector system (Clontech). To obtain the human Tie clones, a PCR fragment encoding the Tie signal sequence was amplified from human Tie cDNA (Partanen, et al., *Mol. Cell. Biol.*, 12: 1698–1707 (1992), incorporated by reference herein) using the primers, 5'-CCCACATGAGAAGCC-3' (SEQ ID NO: 4) and 5'-TGAGATCTGGAGTATGGTCTGGCGGGTGCCC-3' (SEQ ID NO: 5), and used to probe the aforementioned library. The resulting positive clone containing the longest insert was plaque-purified and an approximately 7 kb SacI fragment was subcloned in pGEM 3Zf(+) and characterized. A partial DNA sequence of the clone is set forth in SEQ ID NO: 2.

A comparison of genomic DNA sequences of mouse and human Tie promoters is shown in FIG. 2. In that Figure, the mouse sequence extends from the 3' end of the first exon to an AflII site which is approximately 821 bp upstream from the ATG codon. A CA repeat found only in the mouse sequence is highlighted in bold in FIG. 2. Two identified transcription initiation sites are marked in FIG. 2 with asterisks (See primer extension and RNAse protection experiments below). Restriction endonuclease cleavage sites discussed herein are marked in bold.

Those portions of the mouse and human promoter sequences having a high level of similarity to each other are preferred portions for use as hybridization probes, to identify Tie promoter sequences from genomic DNA of other mammalian species. For conventional hybridization techniques, portions comprising at least about 18 nucleotides are preferred, and are intended as aspects of the invention.

EXAMPLE II

Determination of The Transcription Initiation Site in The Human Tie Gene

For primer extension analysis of Tie-encoding nucleic acids, primer was labelled according to the manufacturer's instructions (Promega, USA). An aliquot of 10 pmol primer was then incubated with 10× forward exchange buffer (Promega), 10 μCi/ml [γ-$^{32}$P]-ATP, and 10U T4 polynucleotide kinase at 37° C. for 1 hour. The kinase was then inactivated by heating at 90° C. for 2 minutes and the labelled primer was ethanol precipitated.

Poly (A+) RNA (20 micrograms, isolated from LE II mouse lung endothelial cells, which are described in Schrieber, et al., *Proc. Natl. Acad. Sci. (USA)*, 82:6138–6142 (1985)) and 5×10$^5$ cpm labelled primer were then annealed in hybridization buffer (40 mM PIPES, pH 6.4, 1 mM EDTA, pH 8.0, 0.4M NaCl and 80% formamide) by heating at 95° C. for 12 minutes. Samples were then cooled slowly and ethanol precipitated. The resulting dried annealing mixture was suspended in primer extension buffer (50 mM Tris-HCl, pH 8.3, 50 mM KCl, 10 mM MgCl$_2$, 10 mM DTT, 2 mM each of deoxy ATP, deoxy CTP, deoxy GTP, and deoxy TTP, 0.5 mM spermidine) and 20 U RNAsin and 40 U AMV reverse transcriptase were added. After 2 hours of incubation at 42° C., template RNA was digested by addition of 20 μg/ml RNAse A in 100 mM NaCl, 10 mM Tris-HCl, 1 mM EDTA, pH 7.4, 37° C. for 15 minutes. The resulting mixture was phenol extracted and ethanol precipitated. The pellet was then resuspended in loading dye (98% formamide, 10 mM EDTA, 0.1% xylene cyanol, 1% bromophenol blue) and loaded onto a 9% polyacrylamide/7M urea gel. After electrophoresis, the dried gels were exposed to x-ray film for 2 days.

RNAase protection was accomplished using mouse RNA antisense probes of 291 bp and 239 bp generated from linearized plasmids containing the 842 bp AflII-BamHI and 1.3 kb HindIII-ApaI mouse Tie promoter DNA inserts. The human RNA probe of 568 bp was generated from linearized pGEM 3Zf(+) plasmid (Promega, USA) containing an AccI-AlwNI human Tie promoter DNA insert. The template for the other human 266 bp RNA probe was generated by PCR amplification from the AccI-AlwNI plasmid. M13 Forward and Tie 2168 primers (marked in FIG. 2) were used for amplification. The probes were labeled using T7 polymerase and [γ-$^{32}$P]-UTP. Ten micrograms of poly A(+) RNA was incubated with labelled probe at 50° C. overnight. Unhybridized RNA was digested with RNAse A (10 U/ml) and T1 (1 microgram/ml) at 37° C., pH 7.5 for 1 hour. The RNAses were inactivated by proteinase K digestion at 37° C. for 15 minutes and the samples were analyzed in 8% sequencing gels.

The primer extension and RNase protection products terminated at positions 101 bp and 116 bp upstream from ATG codon, in mouse and human Tie promoters, respectively (see asterisks in FIG. 2). Yeast tRNA or NIH 3T3 RNA did not show any specific bands. Results are shown in FIG. 2, wherein the sequences of primers referred to above are underlined.

EXAMPLE III

Construction of plasmids

Tie promoter/luciferase gene constructs were generated by subcloning the 5' flanking 788 bp genomic AflII-ApaI fragment located upstream of the ApaI restriction site in the first exon to the promoterless basic pGL2 vector (Promega) as described by deWet, et al., *Mol. Cell. Biol.*, 7: 725–737 (1987), incorporated by reference herein, resulting in plasmid 0.73mpromGL2. This plasmid was deposited with the ATCC as vector 0.73mTIEpromGL2, having ATCC accession number 75892.

Figure 8:
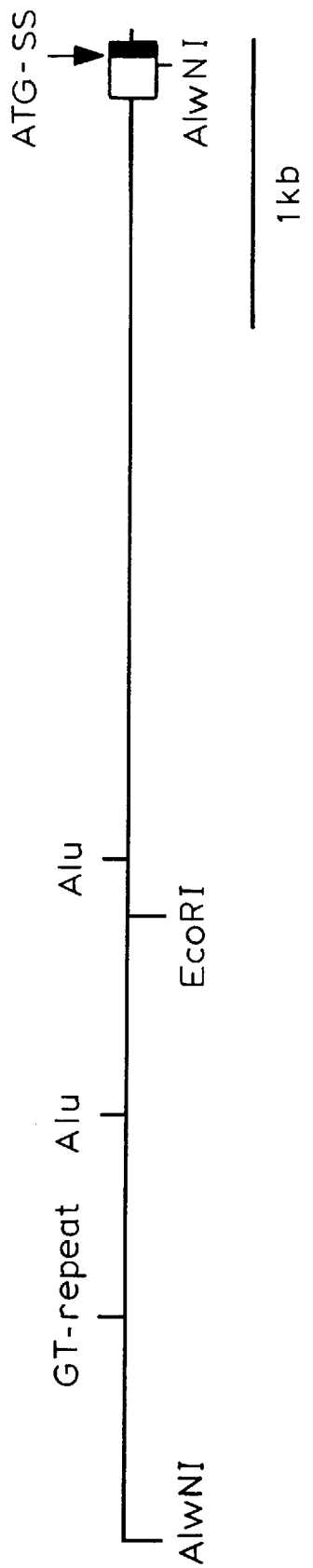
FIG. 8 depicts a partial restriction map of approximately 5 kb of DNA comprising the 5' region of the human Tie gene. Two AlwNI restriction sites, an EcoRI restriction site, and Alu and GT repeat sequences are shown. Shaded and unshaded boxes represent translated and untranslated sequences, respectively. The ATG translation initiation codon and signal sequence (SS) also are depicted.

For experiments in transgenic mice, the pBluescript II KS (+/-) plasmid (Stratagene) was modified by converting the unique SacI site of the polylinker to a SalI site. Then, the 3.6 kb SDKLacZpA cassette described in Logan et al., *Development*, 117:905–916 (1993) (incorporated by reference herein) was cloned as a blunt-ended HindIII-BamHI fragment into the blunted ClaI site of the resultant modified pBluescript II KS (+/-) plasmid, so that the unique HindIII site of this plasmid was located upstream of the LacZ open reading frame. The 788 bp AflII-ApaI promoter fragment (shown in FIG. 2) was then blunt-end ligated into the blunted, unique HindIII site in the resultant vector. The correct orientation of the Tie promoter insert (same as SDK-LacZpA) was confirmed by sequencing. This cloning resulted in vector 0.73mpromSDK-LacZ, referred to alternatively as 0.73mTIEpromLacZ and 0.73mTIEpromSD-KLacZ. Similarly, a 5 kb AlwNI fragment (FIG. 8) of the ~7 kb human Tie promoter clone described in Example I (a partial sequence of which is shown in FIG. 2) was blunt-end ligated into the SDK-LacZpA Bluescript vector, resulting in plasmid 5.0hTIEpromSDK-LacZ. This plasmid was deposited with the American Type Culture Collection, 12301 Parklawn Drive, Rockville, Md. 20852, and given ATCC Accession Number 75893.

EXAMPLE IV

DNA transfection and preparation of cell lysates

Fifteen micrograms of the 0.73mpromGL2 plasmid described above was transfected into either LE II mouse lung endothelial cells, which are described in Schrieber, et al., *Proc. Natl. Acad. Sci. (USA)*, 82: 6138–6142 (1985), incorporated by reference herein, or MK-2 mouse epithelial cells, described by Weissman, et al., *Cell*, 32: 599–606 (1983), incorporated by reference herein. Transfection was accomplished using the modified calcium phosphate mediated transfection method reported in Sambrook, et al. (eds.), *Molecular Cloning: A Laboratory Manual* (1989) incorporated by reference herein. The DNAs were mixed with 0.25M CaCl$_2$ and an equal volume of 50 mM N,N-bis(2-hydroxyethyl)-2-aminoethane sulfonic acid-buffered saline. The mixture was incubated for 15 minutes at room temperature and then added dropwise on growing cell monolayers.

The resulting cultures were incubated for 12 hours, after which 5% glycerol in PBS (phosphate buffered saline) was added for 30 seconds and washed off with two changes of PBS. Fresh medium was then added. After further incubation for 24 hours, the cells were lysed in 0.5 ml lysis buffer (25 mM Tris-PO4, 2 mM dithiothreitol (DTT), 2 mM 1,2-diamino-cyclohexane, N,N,N',N'-tetracetic acid, 10% glycerol, 1% Triton X-100, pH 7.8). The resulting lysates were centrifuged and the supernatants were collected and stored at -70° C. until further assayed. Normalization of luciferase values relative to transfection efficiency was achieved by cotransfection of a CMV-β-gal vector described in MacGregor and Caskey, *Nucl. Acids. Res.*, 17: 2365 (1989), incorporated by reference herein.

Assays for β-galactosidase and luciferase were conducted on transfected cells. For the β-galactosidase assay, 30 ml of the cell lysate described above was incubated in 33 ml of o-nitrophenyl-β-D-galactopyranoside (4 mg/ml) dissolved in 100 ml 0.1M sodium phosphate, pH 7.5, for 30 minutes at 37° C. Optical density was measured at 414 nm.

Luciferase assays were performed using a FlyLight monitoring Kit (102-100, BioTools, Finland) according to the manufacturer's protocol. Briefly, 20 ml of cell lysate was incubated in 100 ml reaction mixture, and a Bio-Orbit 1253 luminometer was used to determine light intensity.

The activity of the Tie promoter in cultured cells was measured using Tie promoter-luciferase constructs described above. The Tie promoter-luciferase constructs were transfected into either LEII endothelial cells or into MK-2 epithelial cells. Promoter activity was determined as the ratio of luciferase to β-galactosidase activity. Those activities were compared to the promoter activity of the positive control vector, RSV-luc (ATCC).

Figure 3:
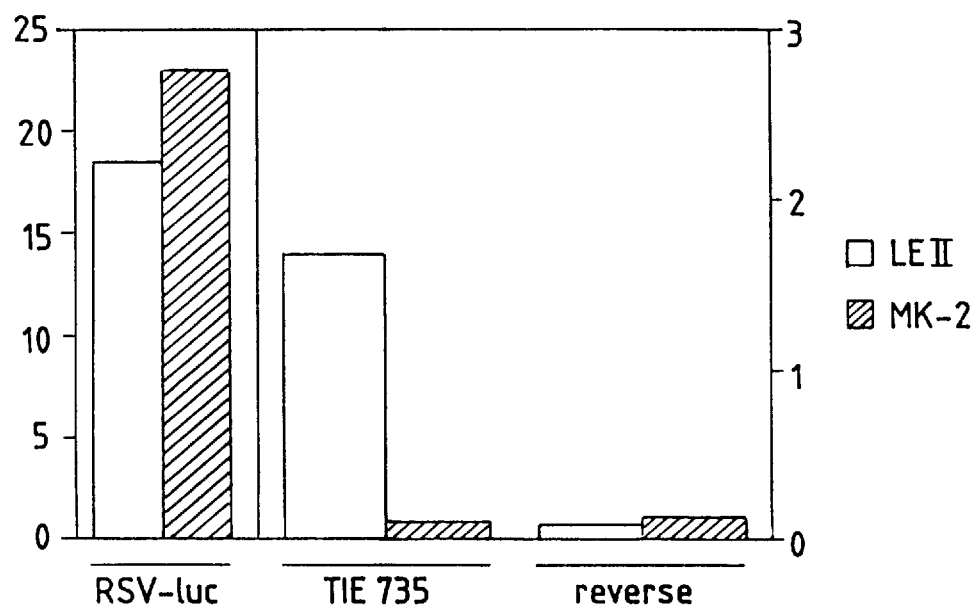
FIG. 3 shows results of an analysis of Tie promoter activity.

Activity of the 0.73mpromGL2 plasmid relative to CMV-β-gal, used as a constitutively expressed cotransfected control promoter, is shown in FIG. 3, along with values for the highly expressed RSV-luc promoter. A 460 bp mouse Tie promoter fragment was used in reverse orientation as a negative control (reverse). As shown in FIG. 3, the Tie promoter was highly active in LEII cells but not in the epithelial cells, MK-2. Those results indicated that the isolated Tie promoter is specific for vascular endothelial cells and efficiently promotes the expression of the reporter in those cells in comparison to the control.

Additional transfection experiments were conducted with both the 0.73mpromGL2 mouse Tie promoter plasmid construct and a construct comprising a ~3 kb EcoRI-AlwNI human Tie promoter fragment (FIG. 8) that was blunt-ended and cloned into the HindIII site of pGL2. Thirty micrograms of the 3 kb human Tie promoter plasmid or an equimolar amount of the mouse Tie plasmid and Rous Sarcoma virus long-terminal repeat-luciferase (RSV-luc) control plasmid (ATCC) were transfected into LE-II mouse lung endothelial cells or HeLa human cervical carcinoma cells as described above.

The promoter activities of the Tie promoter plasmids were compared to the promoter activity of RSV-luc. After normalizing for the intracellular copy number of the trnasfected plasmids, both the mouse and human Tie promoter constructs yielded 6% to 15% of the activity obtained with the strong RSV promoter in LE-II and HeLa cells. In inverse orientation, the Tie promoter constructs showed very little activity. The Tie promoter also was active in transfected K562 human leukemia cell lines, indicating a lack of endothelial cell-specificity in these transfected cell lines.

EXAMPLE V

Production of transgenic mice

The Tie-containing transgene was separated from the vectors described in Example III by digestion with SalI, purified by electrophoresis through an agarose gel, and recovered by absorption on glass beads (Gene Clean II, Bio 101 Inc., La Jolla, Calif.) according to the manufacturer's instructions. Transgenic mice were produced by the standard microinjection technique reported in Hogan et al., *Manipulating the mouse embryo* (Cold Spring Harbor, 1986), incorporated herein by reference. Zygotes for microinjections were obtained from superovulated (BALB/c×DBA/2)F1 hybrid female mice (CD2F1) mated with CD2F1 males. Alternatively, eggs used for injection were from randomly bred superovulated CD1 females. After microinjection, zygotes were transferred at the one or two cell stage into oviducts of pseudopregnant foster mothers (CD2F1 mice). Tail samples were taken from mouse pups at three weeks of age and DNA was isolated from the samples by the salt precipitation method of Miller, et al., *Nucl. Acids. Res.*, 16: 1215 (1988), incorporated by reference herein. The polymerase chain reaction was used to confirm the presence of the transgene in the transgenic mice using the mouse promoter-specific primer, 5'-CTATTGAGAAGGTTTGGAGGC-3'[SEQ ID NO: 6], the lacZ primer, 5'-GCTCTAGAACTAGTGGATC-3'[SEQ ID NO: 7]; the human promoter-specific primer, 5'-GAGACAGGGGATGGGAAAAA-3'[SEQ ID NO: 8]; and the lacZ primer, 5'-GAAGATCGCACTCCAGCCAG-3' [SEQ ID NO: 9] using a reaction mixture comprising 200 ng DNA (Tail), 10× buffer (2 mM $MgCl_2$), 250 nM Primer 2040 [SEQ ID NO: 6], 250 nM Primer 1986 [SEQ ID NO: 7], 0.2 mM dNTP Mixture, 0.02 U Dynazyme(Finnzymes, Finland), and 50 ml of distilled water, plus 50 ml mineral oil (M-3516; Sigma, USA). The PCR Program consisted of a hot start at 96° C., 2 minutes, with cycling as follows: 96° C. 1 minutes, 50° C. 2 minutes, 72° C. 3 minutes, for 34 Cycles, with the last step delayed 10 minutes. Six transgenic mice were obtained.

EXAMPLE VI

Analysis of Tie-containing Tissue

Eight-week old transgenic males were mated with wild-type NMRI females and the offspring (86 for 788 bp mouse Tie fragment construct and 47 for 5.0 kb human Tie fragment construct) were analyzed on days 7.5–17.5 of development.

Whole mouse embryos were obtained and stained for β-galactosidase activity. Tissue was transferred into 4% paraformaldehyde in PBS (pH 7.4) and incubated at 4° C. for 20 minutes with gentle agitation. Tissue was then washed with PBS and incubated in fresh X-Gal reaction mixture [1 mg/ml 4-chloro-5-bromo-3-indolyl-β-galactoside, 4 mM $K_4Fe(CN)$ $6\times3H_2O$, 2 mM $MgCl_2$ in PBS] at 30° C. for 1 to 2 days. Then, samples were washed in PBS for 5 hours and transferred to 30% sucrose for storage.

Samples were then embedded in Tissue Tek (Miles, USA) and 15 μm sections were cut on silane-treated slides. Sections were post-fixed in 4% paraformaldehyde for 5 minutes, and washed twice in PBS and once in distilled water. Nuclear fast red was applied as a counterstain.

Of the F1 offspring, 40% were positive in LacZ staining, although the embryos showed a variation of the intensity of the reaction color. No staining was seen in 7.5 day post-coital embryos, whereas in 8.5 day post-coitum embryos, endothelial cells of the dorsal aorta and forming heart were strongly positive. Certain cells of the head mesenchyme, presumably differentiating angioblasts, showed a faint signal, and the extraembryonic tissues, such as allantois and yolk sac, contained positive vessels.

Figure 4A:
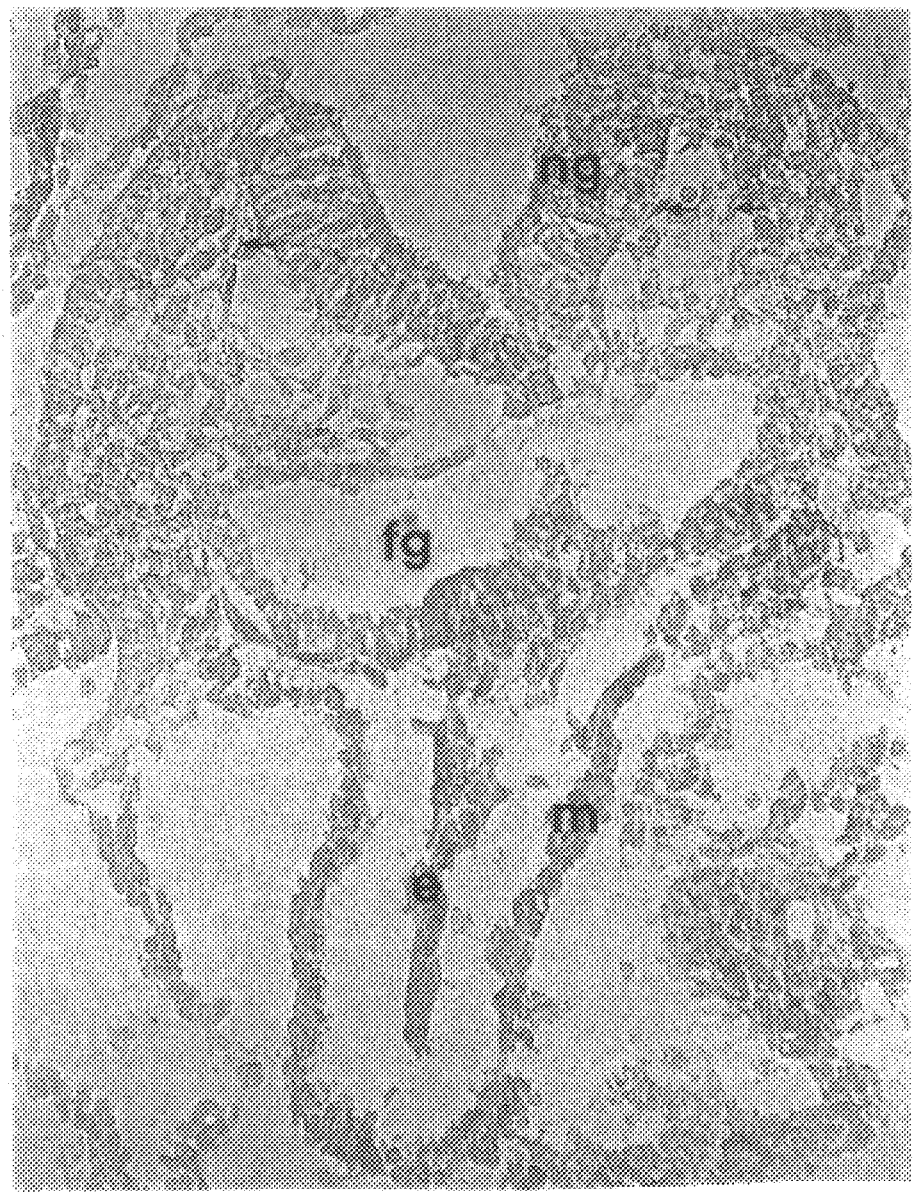
FIG. 4, panel A, shows expression patterns of the Tie promoter in the developing endocardium and head mesenchyme of 8.5 day mouse embryos.
Figure 4B:
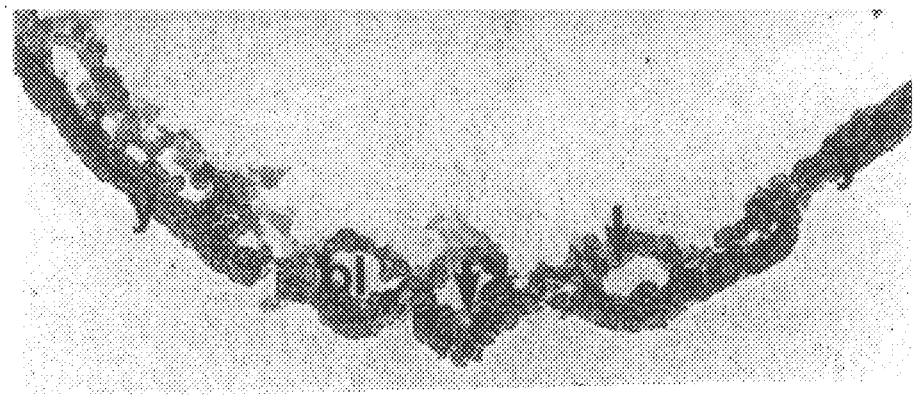
Figure 5A:
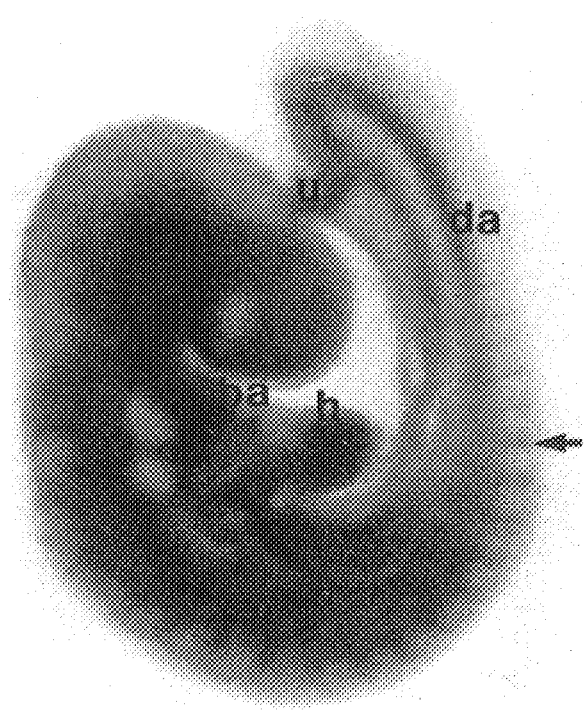
FIG. 5, panels A and B, show the expression pattern of mouse Tie promoter in 9.5 day embryos.
Figure 5B:
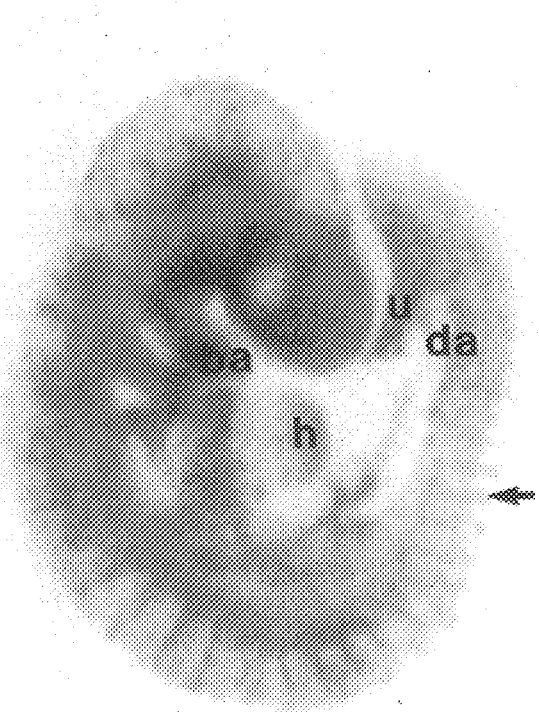
Figure 5C:
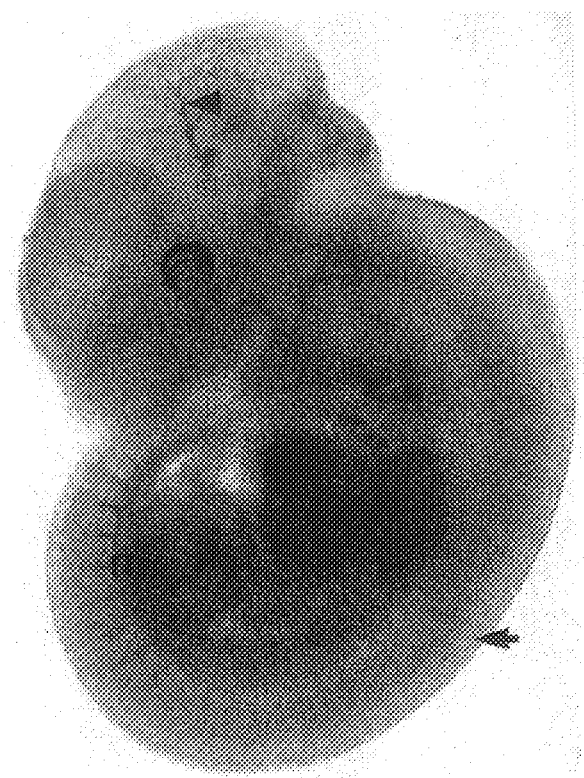
Figure 5D:
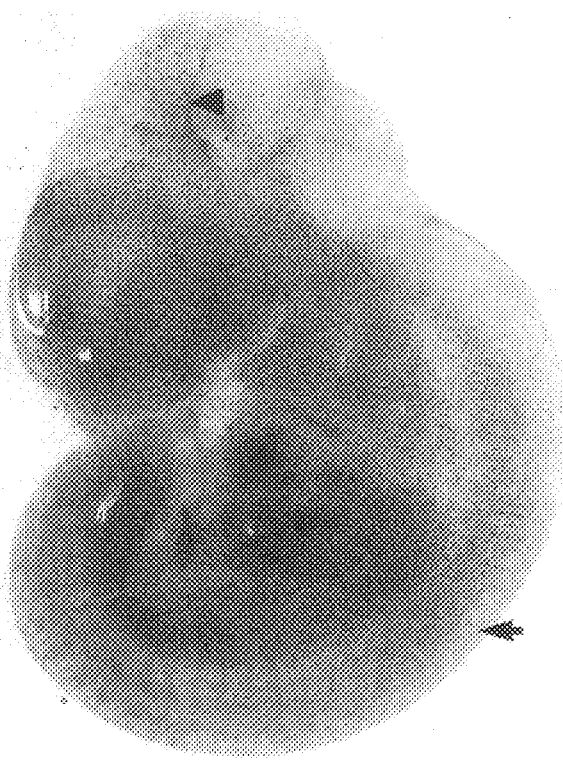
Figure 6A:
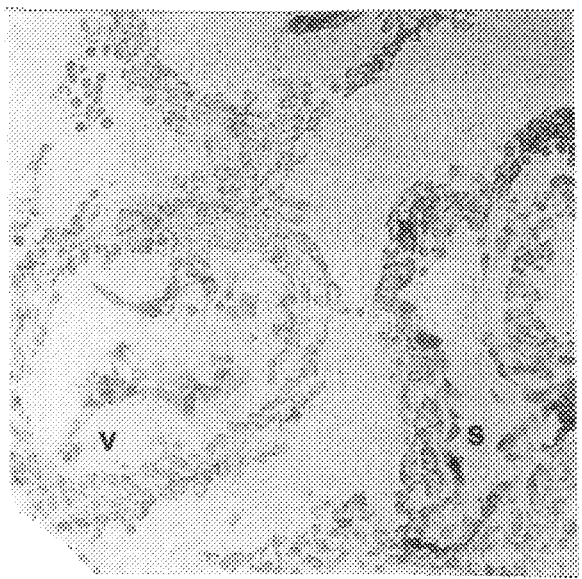
FIG. 6, panel A, shows expression of the Tie promoter in 9.5 day embryonic heart tissue.
Figure 6B:
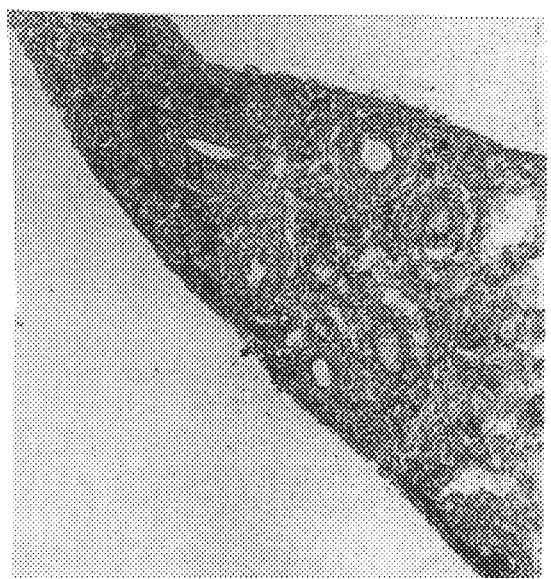
Figure 6C:
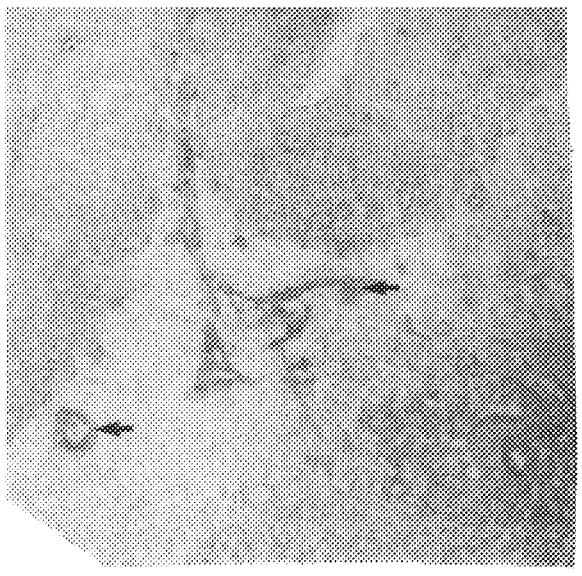
Figure 6D:
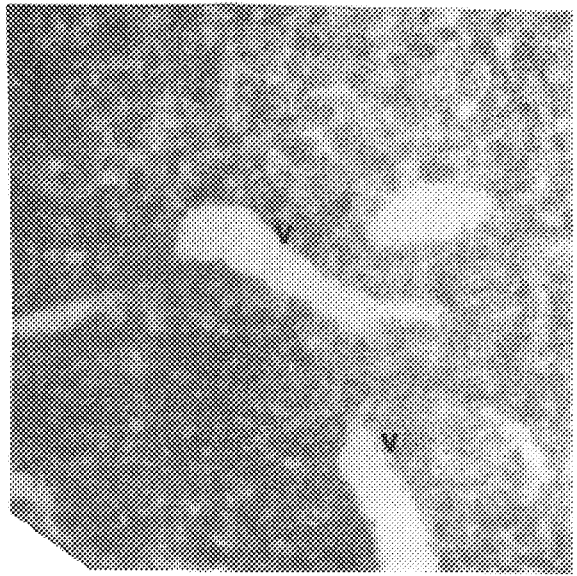
Figure 6E:
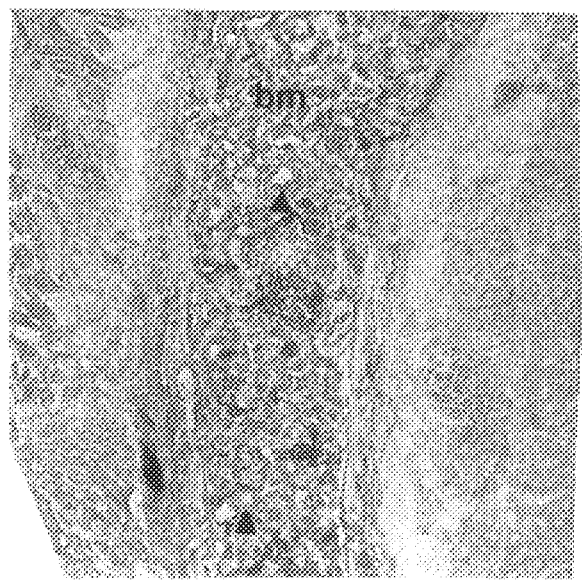
Figure 6F:
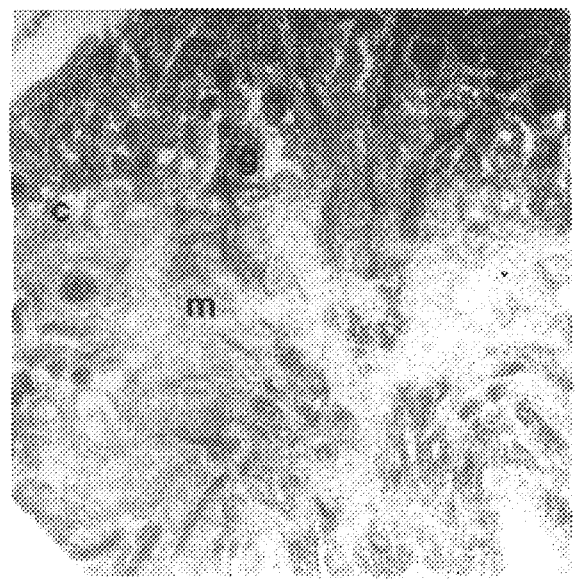
Figure 7A:
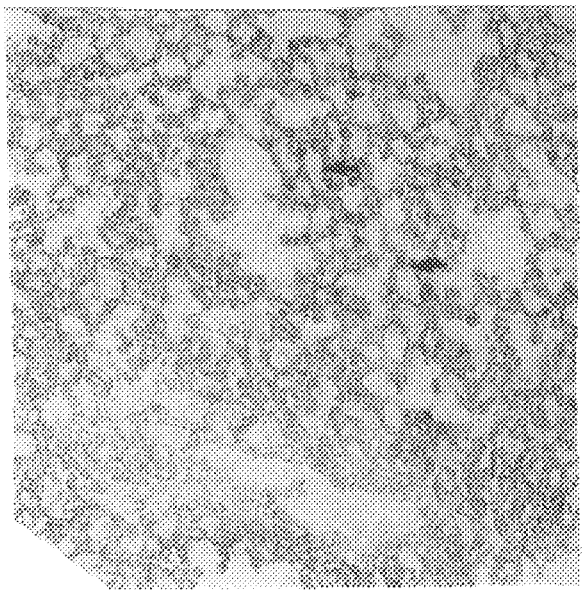
FIG. 7, panel A, shows expression of the Tie promoter in the interalveolar capillaries of the lung in an 8-week-old mouse.
Figure 7B:
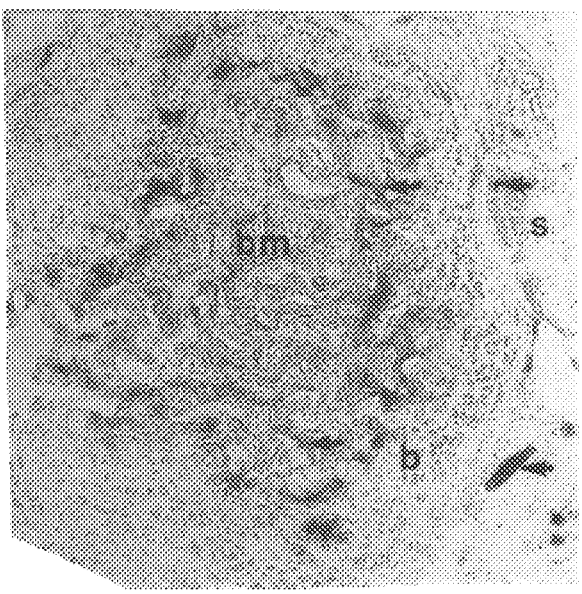
Figure 7C:
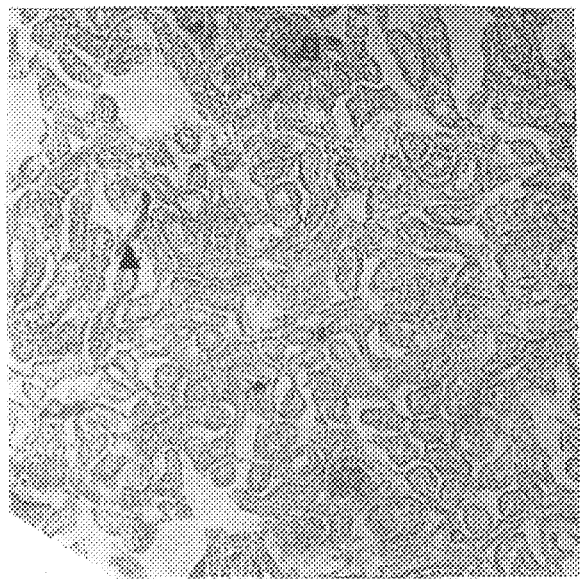
Figure 7D:
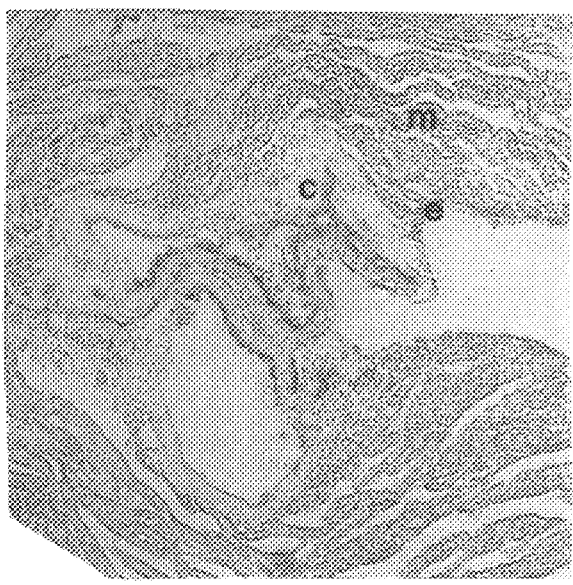
Figure 7E:
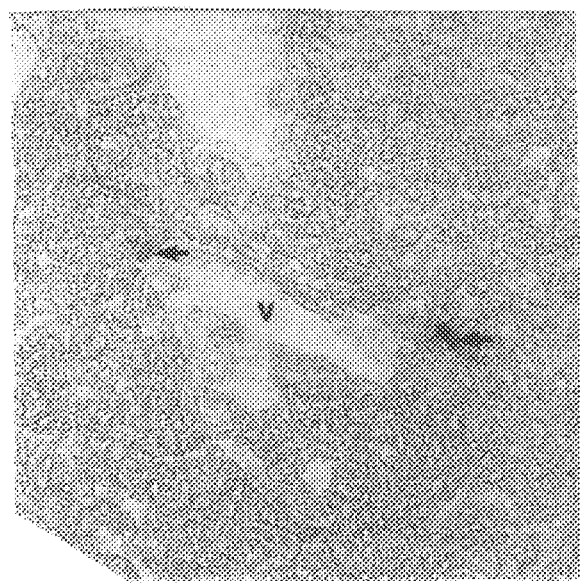
Figure 7F:
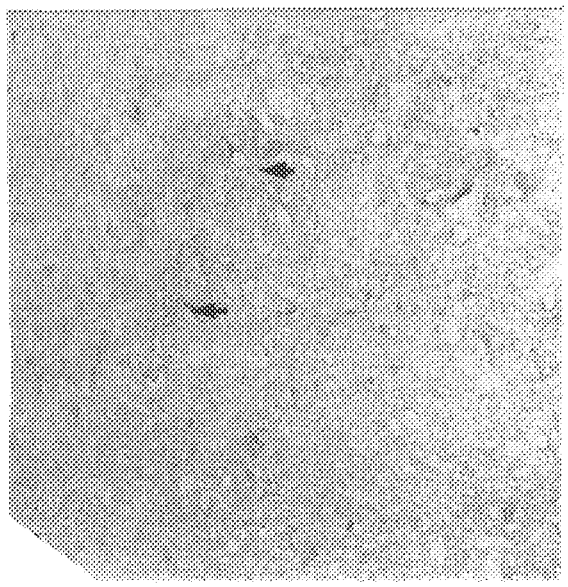

The complexity of the vascular system increases rapidly in the developing embryo, and in 9.5 day post-coitum embryos promoter activity was seen in the above mentioned vessels as well as in the intersomitic arteries. An especially intense staining was seen in the developing ventricles of the heart. In 11.5 day post-coital embryos, the capillary system is well-developed, and therefore the staining associated with large vessels of the embryo and the endocardium was only faintly discerned through the dense network of blue-stained capillaries. The details of vascular system were better visualized in high magnification of tissues of day 11.5 and 15.5 post-coital embryos. That staining pattern corresponds to the expression pattern obtained in in situ hybridization. As shown in FIG. 4, Panels A and B, the endocardium of the heart, the veins and the arteries of the head mesenchyme showed LacZ signal. No significant differences were seen in the staining patterns obtained with mouse 788 bp and human 5.0 kb promoter fragment constructs.

Additional results are provided in FIGS. 5 and 6. FIG. 5, panels A–D, show expression of the mouse Tie promoter in 9.5 (Panels A and B) and 11.5 (Panels C and D) day post-coitum mouse embryos. As seen in the figures, activity of the β-galactosidase reporter gene is found in the developing heart (h), branchial vessels (ba), paired dorsal aorta (da), vitelline artery (v), umbilical artery (u), and in capillaries (c) of 9.5 day post-coitum embryos. Two days later (FIG. 5, Panels C and D), a similar pattern is found with the addition of staining in the mesonephros (m) and the veins of the liver (l).

FIG. 6, Panels A through F, show Tie promoter activity in 9.5, 11.5, and 13.5 day post-coitum embryos. All endothelial cells of the cardiac region are stained, indicating expression under control of the promoter. Staining is observed in lung, but the bronchi are negative. Brain tissue of 15.5 day embryos also shows staining. FIG. 6, Panel D, shows that the promoter is expressed in veins of the liver and FIG. 6, Panel E, shows staining in the developing bone trabeculae. The developing cortex of the kidney shows staining, expression being most prominent in the glomeruli.

In order to determine if the promoter activity of the 788 bp mouse fragment correlates with expression of Tie mRNA in adult tissues, various tissue types obtained from 8-week old transgenic mice were stained for β-galactosidase activity. As shown in FIG. 7, Panels A and B, intense staining was observed in lung (FIG. 7, Panel A) and bone marrow (designated bm in FIG. 7, Panel B). FIG. 7, Panel B, also shows staining in capillaries associated with hair follicles (designated by the arrow in FIG. 7, Panel B). Slightly less staining was observed in kidney glomeruli (FIG. 7, Panel C, designated "g") and vessels surrounding the tubuli (FIG. 7, Panel C, designated by the arrowhead). FIG. 7, Panel D, shows staining in the endocardium. Neither large hepatic vessels (v in FIG. 7, Panel E) or sinusoidal capillaries (not shown) stained with LacZ in adult mice. However, small vessels surrounding the veins did stain [Arrows in FIG. 7, Panel E]. As shown in FIG. 7, Panel F, interstitial capillaries of the brain were stained [Arrowheads in FIG. 7, Panel F]. Similar results were obtained when transgenic mice expressed the 5 kb human Tie promoter construct.

The foregoing results are in agreement with the results of in situ hybridization of Tie mRNA in adult tissues, including down-regulation of Tie expression in certain tissues after development. Thus, the Tie promoter comprises an endothelial cell-specific promoter which retains activity in adult mice, in contrast to the tek promoter, which appears to be shut off during embryonic development. See Schlager et al., *Development*, 121:1089 (1995).

EXAMPLE VII

Localization of Tie Promoter Activity

To further characterize the Tie promoter and identify portions thereof having promoter activity, fragments of the promoter sequences provided herein are cloned (e.g., using restriction digestions, exonuclease digestions, PCR amplification, and/or other known techniques) and assayed for promoter activity as described in the preceding examples.

Figure 9:
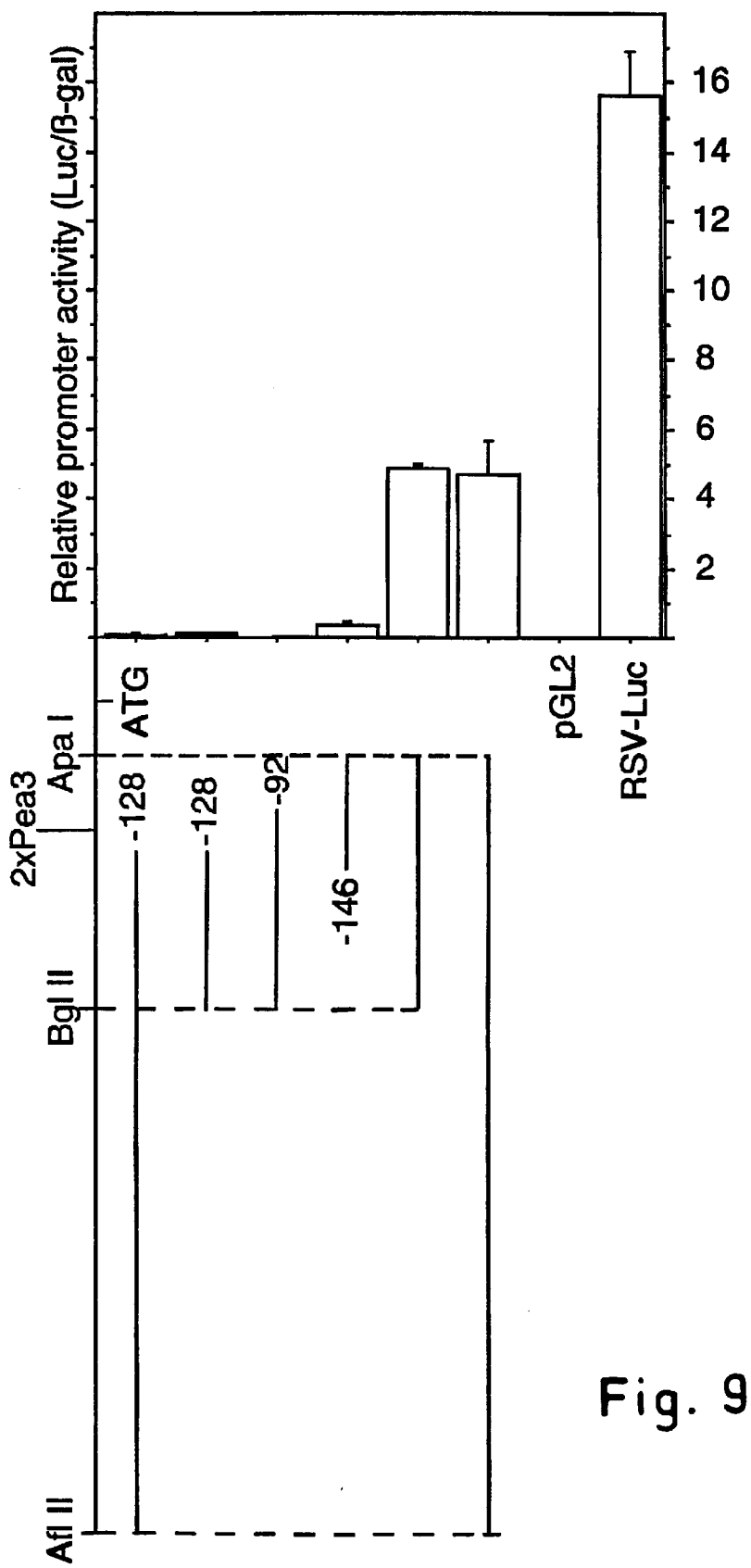
FIG. 9 depicts a partial restriction map of the mouse Tie promoter sequence shown in FIG. 2, from an AflII restriction site to the ATG translation initiation codon. The locations of six fragments of the mouse Tie sequence are schematically depicted beneath the restriction map. Numbers adjacent to end(s) of fragments indicate distance upstream from the ATG translation initiation codon. A bar graph adjacent to the fragments depicts the promoter activity of each fragment in transfected LE II cells, relative to the promoter activity of the strong RSV promoter in transfected cells.

For example, subfragments of the AflII-ApaI mouse Tie promoter fragment described in Example III were generated using well-known techniques and then cloned into the pGL2 vector (Promega). FIG. 9 depicts the size and location of six fragments that were generated. Mouse LE II lung endothelial cells were transfected with these Tie promoter-pGL2 clones and assayed for promoter activity, using procedures described in Example IV. As controls, pGL2 vector without any insert and the RSV-luc plasmid were employed.

The bar graph in FIG. 9 depicts the promoter activity of each clone in transfected LE II cells, relative to the promoter activity of the strong RSV promoter. Importantly, a BglII-ApaI fragment (corresponding to nucleotides 1274 to 1517 of SEQ ID NO: 1) demonstrated a comparable level of promoter activity to the AflII-ApaI fragment (SEQ ID NO: 1, nucleotides 730 to 1517). In contrast, a BglII-ApaLI fragment (FIG. 9, fragment ending at position −92) (SEQ ID NO: 1, nucleotides 1274 to 1462) did not demonstrate promoter activity. An ApaI fragment with its 5' end 146 bp upstream from the ATG initiation codon (SEQ ID NO: 1, nucleotides 1408 to 1517) demonstrated markedly reduced promoter activity.

The promoter activity of the BglII-ApaI fragment was demonstrated in transgenic mice. An SDK-LacZ construct incorporating this fragment was generated by digesting plasmid 0.73mTIEpromSDKLacZ (Example III) with AflII and BglII, filling in the "sticky ends," and religating the resultant blunt-end SDK-LacZ construct (SEQ ID NO: 1, nucleotides 1274 to 1517). Transgenic mice were created using this construct essentially as described in Example V.

Figure 10:
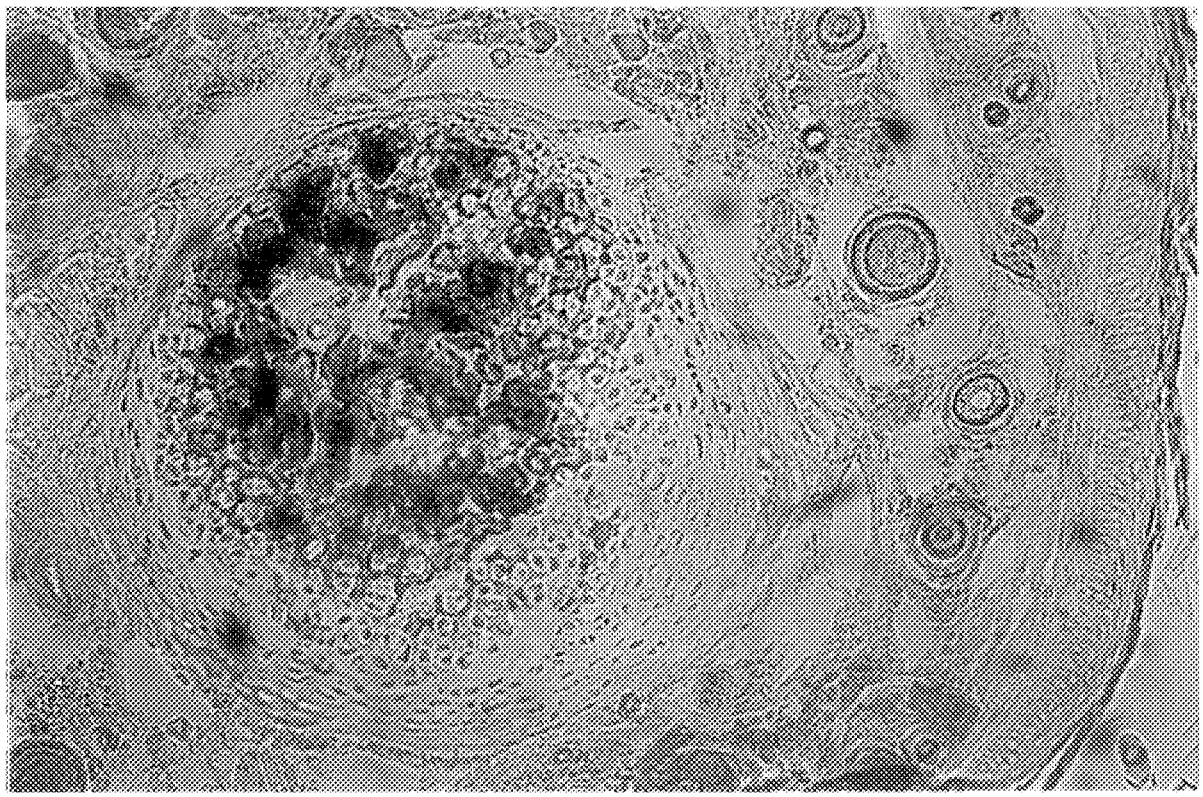
FIG. 10 shows expression of a BglII-ApaI mouse Tie promoter/β-galactosidase chimeric gene construct in bone marrow tissue of an eight week old transgenic mouse.

Tissue analysis of the resultant adult transgenic mice showed that the BglII-ApaI subfragment promoted β-galactosidase activity mainly in the bone marrow (FIG. 10) and lung. Endothelial cells in the skin were negative for β-galactosidase staining. The foregoing results indicate a utility for the BglII-ApaI fragment for targeting gene expression in, e.g., bone marrow and/or lung.

Repetition of the foregoing procedures to analyze the promoter activity of other fragments will result in identification of additional useful promoter DNAs, all of which are contemplated to be within the scope of the invention. For example, exonuclease digestion and/or PCR amplification using custom primers is performed to generate subfragments of the BglII-ApaI fragment, to further localize the portions of that fragment responsible for promoter activity. Exonuclease digestion and/or PCR amplification using custom primers also is performed to generate subfragments of the AflII-ApaI fragment, to further localize the portions of that fragment responsible for promoter activity in endothelial cells in transgenic mice.

Furthermore, fragment analysis as described in this example using the human Tie promoter constructs described herein will further localize the portions of the human DNA necessary for promoter activity. Due to the high degree of similarity in the human and mouse sequences shown in FIG. 2, it is expected that a fragment of the human DNA corresponding to the mouse AflII-ApaI fragment (e.g., a fragment comprising from about nucleotide 1 to about nucleotide 841 of SEQ ID NO: 2) possesses promoter activity in endothelial cells; and that a fragment of the human DNA corresponding to the mouse BglII-ApaI fragment (e.g., a fragment comprising from about nucleotide 600 to about nucleotide 841 of SEQ ID NO: 2) possesses promoter activity in bone marrow and lung cells.

EXAMPLE VIII

Figure 11:
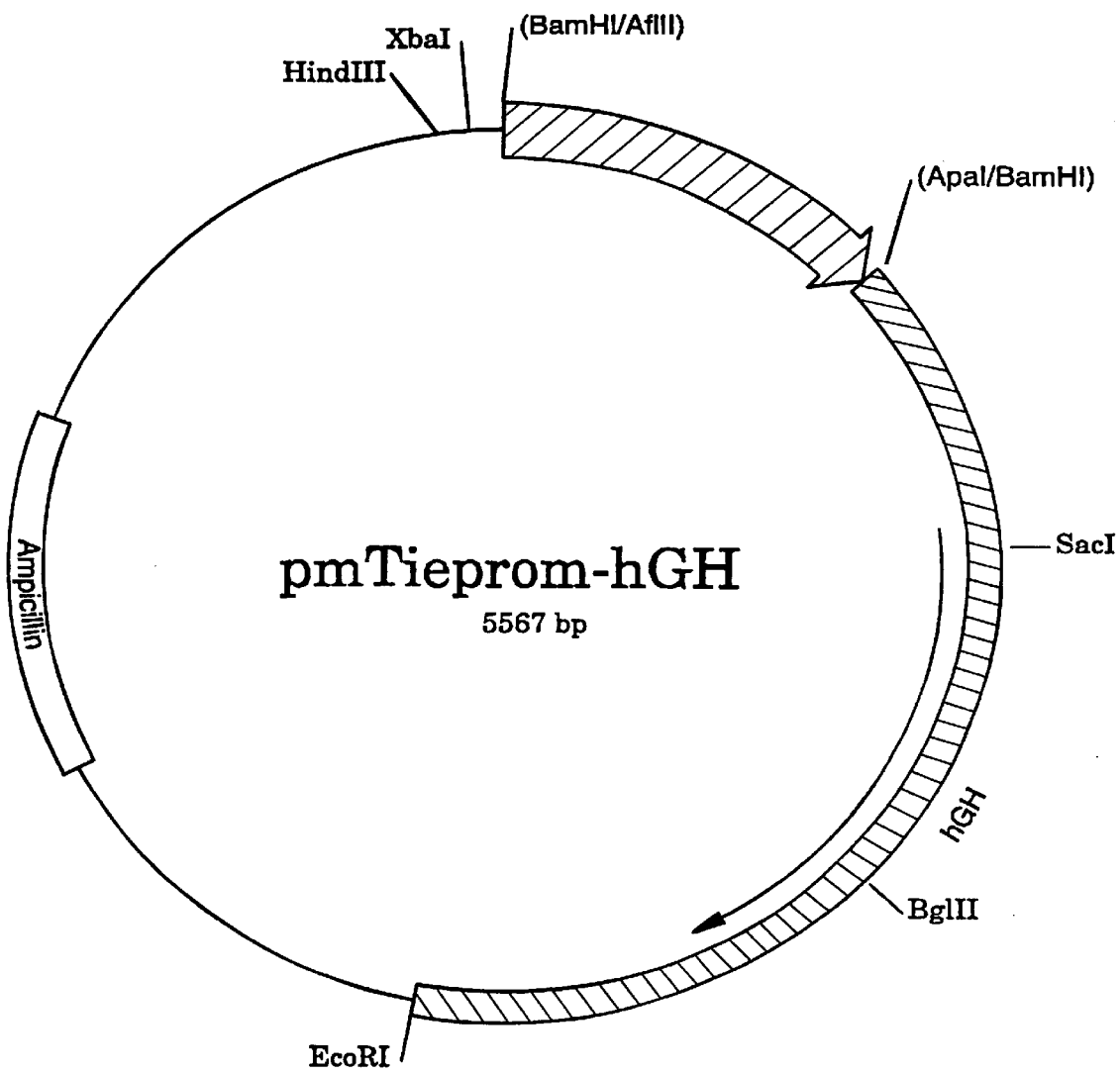
FIG. 11 depicts the construction of plasmid pmTieprom-hGH.

Use of a Chimeric Gene Comprising the Tie Promoter to Promote Growth Hormone Expression in Transgenic Mice The mouse Tie promoter was cloned, as a blunt-ended 788 bp AflII-ApaI fragment, into the blunt-ended BamHI site in pΦGH, containing the human growth hormone (hGH) gene with introns and pA site (Allegro TM HGH Transient Gene Expression Assay System (Nichols Institute, Los Angeles Calif.; see also Selden et al., Mol.Cell.Biol., 6:3173–3179 (1986))). The resulting construct, called pmTieprom-hGH, is depicted in FIG. 11. The pmTieprom-hGH construct was sequenced through the mouse Tie promoter-hGH junction to confirm insertion of the Tie promoter in the correct orientation. Sequencing was conducted with mouse Tie promoter primer 5'-CCCTGCCACCCCTCCTACCC-3' (SEQ ID NO: 10). The promoter-HGH gene junction sequence obtained: 5'-CCACTCAGGG TCTGTGGACA GCTCACCTTA GCT-GCAATGG CTACAGGTAA GC-3' (SEQ ID NO:: 11) was almost identical to the hGH GenBank J00148 sequence.

For generating transgenic mice, the mTieprom-hGH construct was modified by removal of unnecessary bacterial sequences. Specifically, the Tie promoter-hGH chimeric gene was excised from the pmTieprom-hGH construct by digesting with EcoRI and HindIII, and was isolated as the larger of the two generated restriction fragments.

The purified Tie promoter-hGH fragment was then injected into mouse zygotes as described in the preceding examples to create transgenic mice. Transgenic mice were identified by Southern hybridization analysis of tail DNA using the BamHI-EcoRI fragment of plasmid pΦGH as the probe.

The hGH values were measured from the serum of four transgenic and one control mouse at 9 weeks of age using a clinical enzyme immunoassay (Department of Clinical Chemistry, Helsinki University Central Hospital). The immunoassay for the human GH does not detect significant amounts of the antigen in mouse blood (0.1 mU/l in two independent determinations), but all transgenic mice had a significantly elevated concentration in their serum, varying from 0.25 to 26 μg/ml, as depicted in the table below. For comparison, using the same assay, the normal values of hGH in sera of healthy humans are in general below 10 μg/ml.

| Human Growth Hormone Measurements | | | | |
|---|---|---|---|---|
| Mouse | 1 (mU/l) | 2 (mU/l) | mean mU/l | μg/ml |
| control | 0.1 | 0.1 | 0.1 | 0.00004 |
| TG-1 | 69,200 | 65,700 | 67,450 | 25.9 |
| TG-2 | 22,900 | 33,600 | 28,250 | 10.9 |
| TG-3 | 3330 | 6940 | 5135 | 1.97 |
| TG-4 | 271 | 321 | 321.5 | 0.25 |

All transgenic mice (founders) obtained were unusually large (giant mice) and did not reproduce despite several attempts, conforming to reported effects of hGH in transgenic mice.

These results demonstrate that the Tie promoter can be used to produce significant amounts of hormones and other possible therapeutic proteins into blood.

The present invention has been described in terms of its preferred embodiments. Accordingly, the invention should be limited only by the scope of the appended claims.

What is claimed is:

1. A purified and isolated DNA comprising a promoter for a mammalian Tie receptor tyrosine kinase.

2. A DNA according to claim 1 wherein said promoter is a promoter for a mouse Tie receptor tyrosine kinase.

3. A DNA according to claim 2 wherein said promoter comprises a nucleic acid sequence shown in SEQ ID NO: 1.

4. A DNA according to claim 2 wherein said promoter comprises a portion of a nucleic acid sequence shown in SEQ ID NO: 1, wherein said portion is capable of promoting transciption of an endothelial cell receptor tyrosine kinase gene operatively linked to said promoter.

5. A DNA according to claim 2 wherein said promoter comprises nucleotides 1274 to 1517 shown in SEQ ID NO: 1.

6. A DNA according to claim 2 wherein said promoter is capable of promoting transcription of a marker gene operatively linked to said promoter in a transfected mouse bone marrow cell.

7. A DNA according to claim 2 wherein said promoter comprises nucleotides 730 to 1517 of SEQ ID NO: 1.

8. A DNA according to claim 2 wherein said promoter is capable of promoting transcription of a marker gene operatively linked to said promoter in a transfected mouse endothelial cell.

9. A DNA according to claim 4 wherein said promoter comprises nucleotides 1408 to 1517 of SEQ ID NO: 1.

10. A DNA according to claim 1 wherein said promoter is a promoter for a human Tie receptor tyrosine kinase.

11. A DNA according to claim 10 wherein said promoter comprises a nucleic acid sequence shown in SEQ ID NO: 2.

12. A DNA according to claim 10 wherein said promoter comprises a portion of a nucleic acid sequence shown in SEQ ID NO: 2, wherein said portion is capable of promoting transciption of an endothelial cell receptor tyrosine kinase gene operatively linked to said promoter.

13. A DNA according to claim 10 wherein said promoter comprises nucleotides 600 to 841 shown in SEQ ID NO: 2.

14. A DNA according to claim 10 wherein said promoter comprises nucleotides 1 to 841 of SEQ ID NO: 2.

15. A DNA according to claim 10 wherein said promoter comprises an approximately 3 kilobasepair portion of an insert of vector 5.0hTIEpromSDK-LacZ, said portion defined by an a 5' EcoRI restriction site and a 3' AlwNI restriction site.

16. A chimeric gene comprising a promoter for a mammalian Tie receptor tyrosine kinase.

17. A chimeric gene according to claim 16 wherein said promoter comprises nucleotides 1274 to 1517 of SEQ ID NO: 1.

18. A chimeric gene according to claim 17 wherein said promoter is operably linked to a reporter gene.

19. A chimeric gene according to claim 16 wherein said promoter is a promoter for a human Tie receptor tyrosine kinase.

20. A chimeric gene according to claim 19 wherein said promoter comprises nucleotides 600 to 841 of SEQ ID NO: 2.

21. A chimeric gene according to claim 20 wherein said promoter is operably linked to a reporter gene.

22. Vector 0.73mTIEpromGL2, having ATCC accession number 75892.

23. A purified and isolated DNA comprising a Tie promoter insert of the vector according to claim 22, said Tie promoter insert being capable of promoting transcription of a protein-encoding DNA operably linked thereto in murine vascular endothelial cells.

24. A purified and isolated DNA comprising a portion of the vector according to claim 22, said portion being capable of promoting transcription of a protein-encoding DNA operably linked to said portion in murine bone marrow cells.

25. Vector 5.0hTIEpromSDK-LacZ, having ATCC accession number 75893.

26. A purified and isolated DNA comprising a Tie promoter insert of the vector according to claim 25, said Tie promoter insert being capable of promoting transcription of a protein-encoding DNA operably linked thereto in vascular endothelial cells.

27. A vector comprising the DNA according to claim 3.

28. A vector comprising the DNA according to claim 11.

29. A host cell transfected with the vector according to claim 27.

30. A host cell transfected with the vector according to claim 28.

31. A host cell transfected with the chimeric gene according to claim 16.

32. A host cell transfected with the chimeric gene according to claim 19.

33. A mammalian embryonic stem cell transfected with a chimeric gene according to claim 16.

34. A murine embryonic stem cell transfected with a chimeric gene according to claim 17.

35. A purified and isolated DNA comprising at least 18 contiguous nucleotides from a nucleotide sequence selected from the group consisting of SEQ ID NO: 1, SEQ ID NO: 2, the nucleotide sequence complementary to SEQ ID NO: 1, and the nucleotide sequence complementary to SEQ ID NO: 2.

36. A purified and isolated DNA according to claim 35 comprising at least 18 contiguous nucleotides from the nucleotide sequence set forth in SEQ ID NO: 1.

37. A purified and isolated DNA according to claim 35 comprising at least 18 contiguous nucleotides from the nucleotide sequence set forth in SEQ ID NO: 2.

* * * * *

UNITED STATES PATENT AND TRADEMARK OFFICE
CERTIFICATE OF CORRECTION

PATENT NO.    : 5,877,020
DATED         : March 2, 1999
INVENTOR(S)   : Kari Alitalo It is certified that error appears in the above-identified patent and that said Letters Patent is hereby corrected as shown below:

Title page,
Item [75], Inventor, insert -- , Jaana Korhonen, Montreal, Canada -- after Finland Signed and Sealed this Twenty-first Day of January, 2003

JAMES E. ROGAN
*Director of the United States Patent and Trademark Office*

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 1611 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TAACTGCTGC  CAGGCAGGCT  GCCGCGGCCC  TGGCAAAGAT  GTTGAGCAAA  GATGGTGGGC      60

CGGAACAGCG  CCATTGCCGA  GGGCGTGTGC  GGTGCCCTCT  TCATTGGGTA  CTGCATCTAC     120

TTCTACTGCA  AAAGGCGGAG  TGACCCCAAC  TTCAAGAACA  GGCTTCGAGA  ACAAAGAAAG     180

AAACAGAAGC  TTGCTAAGGA  GAGAGCTGAG  TTTTCCAAGT  TTCCTGATTT  AAAAGACGCT     240

GAAGCAGTTC  AGAAATTCTT  CCTTGAAGAG  ACACAGCTTG  GTGAAGGGTT  ATTAGCACAA     300

GGTGACTACG  AGAAGGGTGT  GGACCACCTG  ACAAATGCCA  TTGCTGCCTC  CGCAGCTGCT     360

GCAAGTGTTC  CAGCAGACTC  TTCCACCACC  AGTGTTCCAG  ATGCTCCTGA  CCAAGCTTCC     420

GACCGTTAGT  CAGAGAACTG  TAAGTGCTCA  GAGCCTGGCT  GACAATGATC  TGGAATGAAC     480

CAGATAACAA  CATAATAAAA  TCTCAGTAAA  ATAATTTAAC  AGTTAGCTTG  GAAGCTGGTC     540

AGCTCTGGGG  AAATCAGGGT  AAATTGTGCT  GTCATGAACT  GTCCCACACT  GACATCGGCC     600

AAAGTGAATA  TGAACTTTGG  TAGATCCAAT  GCCTGTTCTA  TTTATTTTTC  CAGTGAAAAG     660
```

-continued

| | | | | | | |
|---|---|---|---|---|---|---|
| TATTTTGATA | GAGCTTTTCA | TTTTGTAAAT | ACACTGAGTT | AACCAAAATA | TCATGGATTT | 720 |
| CCGTTTGTTC | TTAAGACATG | CAACTCGTCT | ACGGCTATAC | CACTCTGAAC | GCGCCCGATC | 780 |
| TCGGAAGACA | TGCAACTCAA | ATGTAAATAC | AGTAGAATAT | TACTTAGGTA | GAAACTCCTG | 840 |
| GTGATTTTAA | AAGATTGGAA | AAGAATATGA | GGAAGAGTTG | AATAATGCAA | ATTCTAGTGT | 900 |
| GTGTGCTACC | GAAGTGAACA | CTTAATGCAC | AGTCTACAGA | CTAGGACATT | TTATCGTGTG | 960 |
| TTGTAAAATT | GGGTAGAAAC | TTGTGTTTGT | GAAAACTGAG | CATTAAAACC | TTACAGAGAC | 1020 |
| CGTTTCTTGT | TTACTTTTGA | AAAAAAAAG | AGTCACGTGA | GCCTCATTTT | GTATTTGTGT | 1080 |
| GTGTGTGTGT | GTGTGTGTCT | CCCCTCCTCC | CAGCGTGTGT | GTGCTGGGAG | GAGGGGAGAC | 1140 |
| CCCAGAACAA | TGTCCTGCCT | CCAAACCTTC | TCAATAGGCG | GAACGACTGG | CTTCCTCCCT | 1200 |
| TTCCTGTCTC | CCGTGCTCCA | GCAATGCAGA | TGGAAGGGAC | CGAAGGGATG | GGAGAGAGAG | 1260 |
| CCCAACCATC | CCCAGATCTG | TCCTTGTCAC | AACCTGCCTC | CCACCTCTAA | TGCCCCCCCT | 1320 |
| TCCAGAGACT | TCCAGGCCAC | ACCCATCCCG | GGCTTGTGGG | GGCTGGACAC | GGGAGGACTA | 1380 |
| CAGGCGACAA | CTCTTCCCAC | CCTCTCTCCC | TGCCACCCCT | CCTACCCTAA | CCATCATTTC | 1440 |
| CTCTTCCTCC | CCAGCACCGA | GGTGCACTGA | GCTGGACAGG | CTGAACACTC | AGACCCACAG | 1500 |
| CAACTGACCC | CGGGCCCAGC | TGGCCTTGGC | TGGCCCAGGG | CAGCTTCCAG | AGTATGGTCT | 1560 |
| GGTGGGGATC | CTCTTTGCTG | CTCCCCACTC | TTTTCTTGGC | CTCTCATGTT | G | 1611 |

( 2 ) INFORMATION FOR SEQ ID NO:2:

( i ) SEQUENCE CHARACTERISTICS:
        ( A ) LENGTH: 935 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| CGGCAAAATG | AATGACACCT | GGCAGACAAT | AAGCTGAAGC | TTTCATTAGC | AGCTTAAGCT | 60 |
| GAGGACTATC | TATGCAACCG | ATACTCCCTG | TGTGCTCCCC | GGGATGGTTA | ATGTGAGGCC | 120 |
| TTGTGGAGCG | ATTGGCACCA | AGGAAAGGAA | GGACTAAGTC | AGAAGTTCAA | GTCCCAGCCT | 180 |
| TGCCACAGCC | TCAGGGTGCC | CTCGAGCACA | GCAAGCCTCA | GTTTTCCCAT | CTGTACAATG | 240 |
| AGAGAGGTAC | ACAAGGTAGA | CTCGAAGGCT | CTTTGTTGCC | AGGGCCCTGT | GTTCCTTTGA | 300 |
| GTGTATGTGC | TTCTCAGGCC | CACAGAGGTC | CTTTGTGTTT | CGTATGTGAA | CTGCTCTCTA | 360 |
| GGAAACCCAT | GTAACTGTCT | GTGTCCTGGG | GCACATACAT | GAGGACTCAT | GTGGGCCGTA | 420 |
| TTGTGTGTTT | GTGCCGGGGG | GAGGGGAGAC | CCCAGAACAA | TGTCCCCCAC | CCCACCCCCC | 480 |
| TCCTCAATAG | GCGAAGCGCA | CTGGCTTCCT | CCCTTTCCTG | CCTCCTGCCT | CCTTTGTGCC | 540 |
| AGCAAGACTG | AGTACTGGAG | GGAGACAGGG | GATGGGAAAA | ATCAGTCCAG | CTGTCCCCAG | 600 |
| GTCTGCCCTT | ACCATAACCT | TCCCCCCACC | TCAAGTGACT | CCTCCCAGGC | CACACCCATC | 660 |
| CCCAGCCTTG | TGGGGGCCAG | ATTGGGGGGC | CTAGAGGCTC | AAAGGCAGAA | TGAGTCCTCC | 720 |
| CACCCCCTAC | CCTGCCACCC | CTCCCACCCA | AGCCACCTCA | TTTCCTCTTC | CTCCCCAGCA | 780 |
| CCGACCCACA | CTGACCAACA | CAGGCTGAGC | AGTCAGGCCC | ACAGCATCTG | ACCCCAGGC | 840 |
| CAGCTCGTCC | TGGCTGGCCT | GGGTCGGCCT | CTGGAGTATG | GTCTGGCGGG | TGCCCCCTTT | 900 |
| CTTGCTCCCC | ATCCTCTTCT | TGGCTTCTCA | TGTGG | | | 935 |

( 2 ) INFORMATION FOR SEQ ID NO:3:

( i ) SEQUENCE CHARACTERISTICS:
  ( A ) LENGTH: 131 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO:3:

| Gly | Cys | Val | Lys | Asp | Cys | Pro | Gly | Cys | Leu | His | Gly | Gly | Val | Cys | His |
|---|---|---|---|---|---|---|---|---|---|---|---|---|---|---|---|
| 1 | | | | 5 | | | | | 10 | | | | | 15 | |
| Asp | His | Asp | Gly | Cys | Val | Cys | Pro | Pro | Gly | Phe | Thr | Gly | Thr | Arg | Cys |
| | | | 20 | | | | | 25 | | | | | 30 | | |
| Glu | Gln | Ala | Cys | Arg | Glu | Gly | Arg | Phe | Gly | Gln | Ser | Cys | Gln | Glu | Gln |
| | | 35 | | | | | 40 | | | | | 45 | | | |
| Cys | Pro | Gly | Thr | Ala | Gly | Cys | Arg | Gly | Leu | Thr | Phe | Cys | Leu | Pro | Asp |
| | 50 | | | | | 55 | | | | | 60 | | | | |
| Pro | Tyr | Gly | Cys | Ser | Cys | Gly | Ser | Gly | Trp | Arg | Gly | Ser | Gln | Cys | Gln |
| 65 | | | | | 70 | | | | | 75 | | | | | 80 |
| Glu | Ala | Cys | Ala | Pro | Asp | His | Phe | Gly | Ala | Asp | Cys | Arg | Leu | Gln | Cys |
| | | | | 85 | | | | | 90 | | | | | 95 | |
| Gln | Cys | Gln | Asn | Gly | Gly | Thr | Cys | Asp | Arg | Phe | Ser | Gly | Cys | Val | Cys |
| | | | 100 | | | | | 105 | | | | | 110 | | |
| Pro | Ser | Gly | Trp | His | Gly | Val | His | Cys | Glu | Lys | Ser | Asp | Arg | Ile | Pro |
| | | 115 | | | | | 120 | | | | | 125 | | | |
| Gln | Ile | Leu | | | | | | | | | | | | | |
| | | 130 | | | | | | | | | | | | | |

( 2 ) INFORMATION FOR SEQ ID NO:4:

( i ) SEQUENCE CHARACTERISTICS:
    ( A ) LENGTH: 15 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:4:

CCCACATGAG AAGCC                                                                                              15

( 2 ) INFORMATION FOR SEQ ID NO:5:

( i ) SEQUENCE CHARACTERISTICS:
    ( A ) LENGTH: 31 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:5:

TGAGATCTGG AGTATGGTCT GGCGGGTGCC C                                                                            31

( 2 ) INFORMATION FOR SEQ ID NO:6:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:6:

CTATTGAGAA GGTTTGGAGG C                                                                                          21

( 2 ) INFORMATION FOR SEQ ID NO:7:

( i ) SEQUENCE CHARACTERISTICS:
          ( A ) LENGTH: 19 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:7:

GCTCTAGAAC TAGTGGATC                                                                                             19

( 2 ) INFORMATION FOR SEQ ID NO:8:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:8:

GAGACAGGGG ATGGGAAAAA                                                                                            20

( 2 ) INFORMATION FOR SEQ ID NO:9:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:9:

GAAGATCGCA CTCCAGCCAG                                                                                            20

( 2 ) INFORMATION FOR SEQ ID NO:10:

( i ) SEQUENCE CHARACTERISTICS:
          ( A ) LENGTH: 20 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:10:

CCCTGCCACC CCTCCTACCC                                                                                            20

( 2 ) INFORMATION FOR SEQ ID NO:11:

( i ) SEQUENCE CHARACTERISTICS:
          ( A ) LENGTH: 52 base pairs
          ( B ) TYPE: nucleic acid
          ( C ) STRANDEDNESS: single
          ( D ) TOPOLOGY: linear ( i i ) MOLECULE TYPE: cDNA ( x i ) SEQUENCE DESCRIPTION: SEQ ID NO:11:

CCACTCAGGG TCTGTGGACA GCTCACCTTA GCTGCAATGG CTACAGGTAA GC                                                        52